(12) United States Patent
Wang

(10) Patent No.: US 8,551,495 B2
(45) Date of Patent: Oct. 8, 2013

(54) ANTI-FMD VACCINE COMPOSITION AND PREPARATION AND USE THEREOF

(75) Inventor: Yu Wang, Beijing (CN)

(73) Assignee: Pharos Vaccine Inc., Seongnam-Si, Gyeonggi-Do (KR)

( * ) Notice: Subject to any disclaimer, the term of this patent is extended or adjusted under 35 U.S.C. 154(b) by 130 days.

(21) Appl. No.: 13/125,907

(22) PCT Filed: Oct. 23, 2009

(86) PCT No.: PCT/CN2009/074585
§ 371 (c)(1),
(2), (4) Date: Apr. 25, 2011

(87) PCT Pub. No.: WO2010/045881
PCT Pub. Date: Apr. 29, 2010

(65) Prior Publication Data
US 2011/0206718 A1      Aug. 25, 2011

(30) Foreign Application Priority Data

Oct. 24, 2008  (CN) .......................... 2008 1 0172927

(51) Int. Cl.
*A61K 39/135*    (2006.01)
*A61K 39/385*    (2006.01)
*C12N 15/62*     (2006.01)
*C07K 19/00*     (2006.01)

(52) U.S. Cl.
USPC ................. 424/192.1; 424/179.1; 424/216.1; 536/23.4; 536/23.72; 530/350

(58) Field of Classification Search
None
See application file for complete search history.

(56) References Cited

U.S. PATENT DOCUMENTS

2002/0076405 A1    6/2002  Yong

FOREIGN PATENT DOCUMENTS

| CN | 1408349 A | 4/2003 |
| CN | 1541710 A | 11/2004 |
| CN | 1616663 A | 5/2005 |

OTHER PUBLICATIONS

Yi et al (Acta Biochimica et Biophysica Sinica 36:589-596, 2004).*
Li et al (Virology 328:274-281, 2004).*
Chan et al (Vaccine 19:538-546, 2001).*
Garcia-Briones et al (Virology 322:264-275, 2004).*
Cedilo-Barron et al (Journal of General Virology 82:1713-1724, 2001).*
Guo et al (Vaccine 23:3236-42, 2005).*
Guo, Hui-chen et al., "Immune reponse of DNA vaccine against foot-and-mout disease virus in cavians enhanced by 3D protein expressed in the Pichia pastoris secreted expression system," Chinese Journal of Veterinary Science and Technology, 2004, vol. 34, No. 03, pp. 12-17; (Cited in ISR, dated Jan. 21, 2010, issued in corresponding PCT/CN20091074585); English Abstract provided.

(Continued)

*Primary Examiner* — Mary E Mosher
(74) *Attorney, Agent, or Firm* — Millen, White, Zelano & Branigan, P.C.

(57) ABSTRACT

The present invention pertains to the field of immunology and genetic engineering. In particular, the present invention relates to the construction, preparation and use of a recombinant vaccine against foot-and-mouth disease virus. The vaccine comprises a tandem repeat of an antigenic epitope of FMDV VP1 protein, the constant region of the immunoglobulin heavy chain or a functional fragment thereof, and the FMDV 3D protein or an immunogenic fragment thereof. The vaccine can induce protective immune response against FMDV in an animal.

28 Claims, 4 Drawing Sheets

(56) References Cited

OTHER PUBLICATIONS

International Search Report, dated Jan. 21, 2010, issued in corresponding PCT/CN2009/074585.
European Search Report from corresponding Application EP09821602 dated Jan. 10, 2013.
T. Collen, et al. "Heterotypic recognition of recombinant FMDV proteins by bovine T-cells: the polymerase (P3Dpol) as an immunodominant T-cell immunogen" Elsevier, Virus Research 56 (1998) pp. 125-133.

* cited by examiner

A

N-terminus [Tandem repeat of an antigenic epitope of FMDV VP1 | Constant region of the immunoglobulin heavy chain | FMDV 3D protein] C-terminus

B

N-terminus [Tandem repeat of an antigenic epitope of FMDV VP1 | Constant region of the immunoglobulin heavy chain] C-terminus N-terminus [FMDV 3D protein] C-terminus

Probed using anti-FMDV anti-serum

ANTI-FMD VACCINE COMPOSITION AND PREPARATION AND USE THEREOF

FIELD OF THE INVENTION

The present invention pertains to the field of immunology and genetic engineering. In particular, the present invention relates to a recombinant vaccine composition against foot-and-mouth disease virus as well as the preparation and use thereof.

BACKGROUND OF THE INVENTION

Foot-and-mouth disease (FMD), the most serious disease among the class A infectious diseases in animals, is a fulminating infectious disease which severely affects cloven hoofed animals such as pig, cattle, sheep and the like. Recently, livestock industries of many countries have suffered huge economical losses caused by the outbreak and epidemic of FMD. So far, seven serotypes of foot-and-mouth disease virus (FMDV) (European A, O and C, African SAT1, SAT2 and SAT3, and Asia 1 serotypes) and many subtypes (see, e.g., Kleid et al., 1981, Science 214: 1125-1129) have been known, with O serotype FMDV being the most widely spread serotype.

FMDV belongs to the *Aphthovirus* genus of the Picornaviridae family. It consists of a positive-sense, single-stranded RNA genome (about 8.5 kb) surrounded by 60 copies of three capsid viral proteins (VP1, VP2, and VP3). Investigations show that in FMDV serotype O, VP1 of these three viral proteins is most relevant to the infectivity of the virus. There are two immunogenic regions in VP1 protein, namely those portions of amino acid residues 141-160 and 200-213. They reside respectively in two protruding, disordered and highly mobile loop structures. The loop structure of the region of residues 145-157 comprises a conserved structure Arg-Gly-Asp (RGD region), involving in the attachment to cell surface receptors (Belsham G J and Martinez-Salas E, Genome organization, translation and replication of foot-and-mouth disease virus RNA, p. 19-52, 2004, Foot and Mouth Disease Current Perspectives, Edited by: Sobrino F and Domingo E). Protein 3D is a RNA-dependent RNA polymerase in FMDV, which has antigenic epitopes recognized by porcine T cells (Belsham G J and Martinez-Salas E, Genome organization, translation and replication of foot-and-mouth disease virus RNA, p. 19-52, 2004, Foot and Mouth Disease Current Perspectives, Edited by: Sobrino F and Domingo E).

Prophylactic immunization can control the transmission of FMDV. Killed virus is used in the existing anti-FMDV vaccines. In practice, such vaccines may cause the transmission of the disease due to the in vivo recombination of the viral RNA (Brown, F. An overview of the inactivation of FMDV and the implications when residual virus is present in vaccines. Dev Biol Stand 1991; 75: 37-41). Meanwhile, chemical inactivating agents are used to inactivate the virus in such vaccines, and low-temperature cold-chain transportation and freezer storage are required during delivery. No freezers are available in the rural areas of some developing countries, and consequently, the vaccines may have substantially lost their efficacy at time of injection. Moreover, the possibility of live FMDV virus leakage during the manufacture process makes the production of such vaccines an unsafe factor for the environment.

The epitope-specific vaccine of the present invention can elicit an antibody response against FMDV in the vaccinated animals. The vaccine of the present invention is not only very safe in use and production, but also very convenient in its handling, storage and transportation. Meanwhile, the vaccine of the present invention can be designed to meet specific requirements.

SUMMARY OF THE INVENTION

The present invention provides a safe and effective recombinant vaccine against FMDV as well as the preparation and the use thereof.

In one aspect, the present invention provides a vaccine composition for inducing a specific immune response against FMDV in an animal, which vaccine composition comprises a recombinant protein comprising from its N-terminus to C-terminus:
 a tandem repeat of an antigenic epitope of the FMDV capsid protein;
 the constant region of the immunoglobulin heavy chain or a functional fragment thereof; and
 the FMDV 3D protein or an immunogenic fragment thereof.

In a further aspect, the present invention provides a vaccine composition for inducing a specific immune response against FMDV in an animal, which vaccine composition comprises:
 (i) a recombinant protein comprising from its N-terminus to C-terminus:
 a tandem repeat of an antigenic epitope of the FMDV capsid protein; and
 the constant region of the immunoglobulin heavy chain or a functional fragment thereof; and
 (ii) the FMDV 3D protein or an immunogenic fragment thereof.

In a preferred embodiment of the vaccine composition of the invention, the antigenic epitope in the recombinant protein is repeated for 2 to 5 times in the tandem repeat. More preferably, the antigenic epitope in the recombinant protein is repeated for 3 times in the tandem repeat.

In one embodiment of the vaccine composition of the invention, the repeated antigenic epitopes are linked to each other via a peptide linker and/or the tandem repeat of the antigenic epitope is linked to the constant region of the immunoglobulin heavy chain via a peptide linker.

In a preferred embodiment of the vaccine composition of the invention, the antigenic epitope is derived from the FMDV capsid protein. The antigenic epitope may be derived from, for example, European A, O and C serotypes; African SAT1, SAT2 and SAT3 serotypes; and Asia 1 serotype. More preferably, the antigenic epitope is derived from the FMDV VP1 protein. In one embodiment of the above mentioned vaccine composition of the invention, the tandem repeat is a tandem repeat of two antigenic epitopes derived from O serotype FMDV VP1 protein, respectively comprising or consisting of an amino acid sequence of SEQ ID NO:9 or SEQ ID NO:10. In a further embodiment of the above mentioned vaccine composition of the invention, the tandem repeat is a tandem repeat of two antigenic epitopes derived from Asia 1 serotype FMDV VP1 protein, respectively comprising or consisting of an amino acid sequence of SEQ ID NO:25 or SEQ ID NO:26. In a further embodiment of the above mentioned vaccine composition of the invention, the tandem repeat is a tandem repeat of two antigenic epitopes derived from A serotype FMDV VP1 protein, respectively comprising or consisting of an amino acid sequence of SEQ ID NO:43 or SEQ ID NO:44. In a further embodiment of the above mentioned vaccine composition of the invention, the tandem repeat is a tandem repeat of three antigenic epitopes derived from bovine O serotype FMDV VP1 protein, respectively comprising or consisting of an amino acid sequence of SEQ ID NO:32, SEQ ID NO:33 or SEQ ID NO:34.

The vaccine composition of the invention may be administered to cloven-hoofed animals such as pigs, cattles, or sheeps, to induce immune response against FMDV infection. Preferably, in the vaccine composition of the invention, the constant region of the immunoglobulin heavy chain contained in the recombinant protein is from the same species as the animal to be vaccinated. The vaccine composition of the invention may further comprise a pharmaceutically acceptable carrier and/or adjuvant.

The present invention also encompasses a recombinant protein as described above.

In a further aspect, the present invention provides an isolated polynucleotide encoding the recombinant protein contained in the vaccine composition of the invention.

The present invention further provides a method of preparing a recombinant protein for use in the anti-FMDV vaccine of the invention, the method comprising the steps of:
  obtaining a polynucleotide encoding the recombinant protein;
  constructing an expression vector containing the polynucleotide;
  introducing the expression vector into a host cell; and
  culturing the host cell under conditions suitable for the expression of the recombinant protein, recovering and purifying the expressed recombinant protein.

In addition, the present invention also relates to a method of preventing FMDV infection in an animal comprising the step of administering an effective amount of the vaccine composition of the invention to an animal in need thereof.

BRIEF DESCRIPTION OF THE DRAWINGS

FIG. 1 illustrates the construction of an anti-O serotype FMDV vaccine of the invention. A: the Vaccine Composition A prepared in the Examples, in which a tandem repeat of an antigenic epitope of the O serotype FMDV VP1 protein, the constant region of animal immunoglobulin heavy chain, and the FMDV 3D protein are linked so as to form a recombinant protein (encoded by "3R-IGCD"). B: the Vaccine Composition B prepared in the Examples, in which a tandem repeat of an antigenic epitope of the O serotype FMDV VP1 protein and the constant region of animal immunoglobulin heavy chain are linked so as to form a recombinant protein (encoded by "3R-IGC"), and the FMDV 3D protein is a separate component.

FIG. 2 shows the Coomassie blue staining of the recombinant protein (encoded by "3R-IGCD") in the Vaccine Composition A of the invention. M: protein molecular weight marker; lane 1: total protein; lane 2: soluble protein; lane 3: inclusion body (dissolved in 6 M urea); lane 4: inclusion body (dissolved in 8 M urea).

FIG. 3 shows the immunoblotting detection of the recombinant protein (encoded by "3R-IGCD") in the Vaccine Composition A of the invention using anti-O serotype FMDV serum. M: protein molecular weight marker; lane 1: total protein; lane 2: soluble protein; lane 3: inclusion body (dissolved in 6 M urea); lane 4: inclusion body (dissolved in 8 M urea).

SEQUENCE LIST

Figure 4:
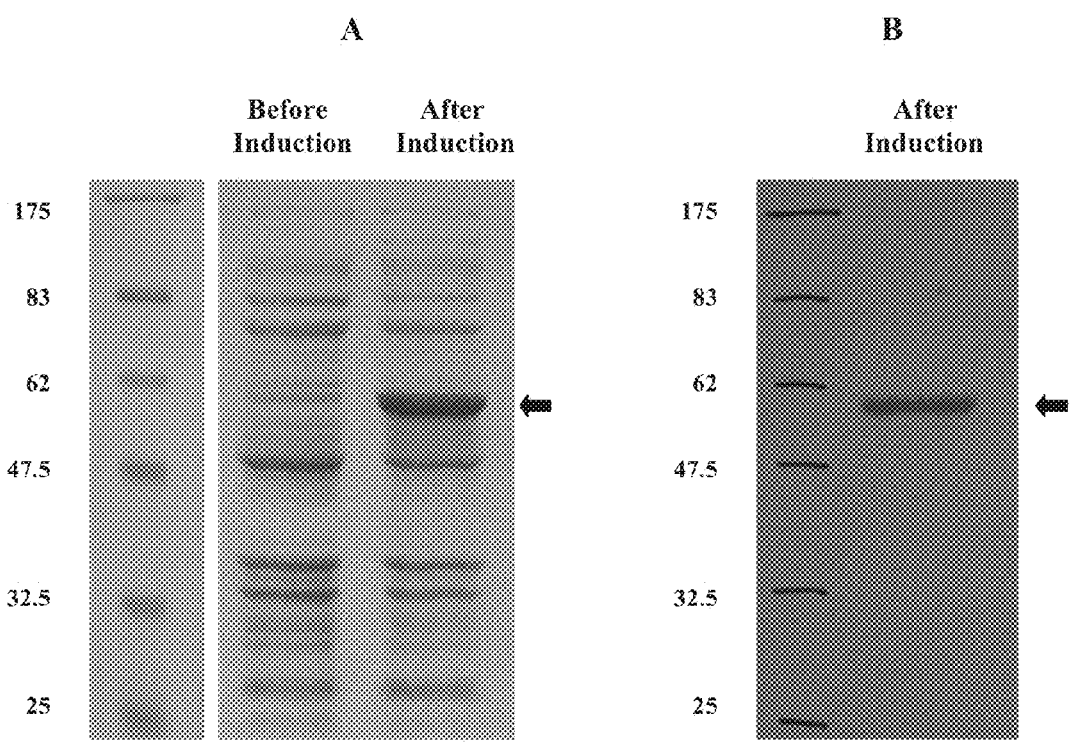
FIG. 4 shows the Coomassie blue staining and immunoblotting detection of the recombinant protein (encoded by "3R-IGC") in the Vaccine Composition B of the invention. A: Coomassie blue staining of the total protein lysate from the bacteria expressing the recombinant protein encoded by the 3R-IGC fragment (before and after IPTG induction); B: immunoblotting detection of the recombinant protein (encoded by 3R-IGC fragment) in the total protein lysate obtained after IPTG induction using anti-O serotype FMDV serum from pig.

SEQ ID NO:1: DNA sequence encoding the tandemly repeated antigenic epitopes of the O serotype FMDV VP1 protein used in the Examples;

SEQ ID NO:2: amino acid sequence of the tandemly repeated antigenic epitopes of the O serotype FMDV VP1 protein used in the Examples;

SEQ ID NO:3: DNA sequence encoding the constant region of porcine immunoglobulin heavy chain used in the Examples;

SEQ ID NO:4: amino acid sequence of the constant region of porcine immunoglobulin heavy chain used in the Examples;

SEQ ID NO:5: DNA sequence encoding the FMDV 3D protein used in the Examples;

SEQ ID NO:6: amino acid sequence of the FMDV 3D protein used in the Examples;

SEQ ID NO:7: DNA sequence ("3R-IGCD") encoding the recombinant protein of the invention used in the Examples;

SEQ ID NO:8: amino acid sequence of the recombinant protein used in the Examples encoded by the "3R-IGCD";

SEQ ID NO:9: amino acid sequence of residues 141-160 of the O serotype FMDV VP1 protein;

SEQ ID NO:10: amino acid sequence of residues 200-213 of the O serotype FMDV VP1 protein;

SEQ ID NO:11: a peptide linker GGSSGG that may be used in the invention;

SEQ ID NO:12: a peptide linker GGGSGGGGS that may be used in the invention;

SEQ ID NO:13: amino acid sequence of the recombinant protein used in the Examples encoded by the "3R-IGC";

SEQ ID NO:14: DNA sequence ("3R-IGC") encoding the recombinant protein of the invention used in the Examples;

SEQ ID NO:15: scIgG 5' primer for amplifying the cDNA fragment encoding the porcine scIgG;

SEQ ID NO:16: scIgG 3' primer for amplifying the cDNA fragment encoding the porcine scIgG;

SEQ ID NO:17: 3D 5' primer for cloning the nucleic acid encoding the FMDV 3D protein;

SEQ ID NO:18: 3D 3' primer for cloning the nucleic acid encoding the FMDV 3D protein;

SEQ ID NO:19: 3R-IGCD 5' primer used for synthesizing the 3R-IGCD fragment;

SEQ ID NO:20: 3R-IGC 3' primer 1 used for synthesizing the 3R-IGCD fragment;

SEQ ID NO:21: D 5' primer used for synthesizing the 3R-IGCD fragment;

SEQ ID NO:22: 3R-IGCD 3' primer used for synthesizing the 3R-IGCD fragment;

SEQ ID NO:23: 3R-IGC 5' primer used for amplifying SEQ ID NO:14;

SEQ ID NO:24: 3R-IGC 3' primer 2 used for amplifying SEQ ID NO:14;

SEQ ID NO:25: amino acid sequence of residues 133-158 of the Asia 1 FMDV VP1 protein;

SEQ ID NO:26: amino acid sequence of residues 200-213 of the Asia 1 FMDV VP1 protein;

SEQ ID NO:27: a peptide linker GGGGS that may be used in the invention;

SEQ ID NO:28: amino acid sequence of the recombinant protein used in the Examples encoded by "3As-IGC";

SEQ ID NO:29: DNA sequence ("3As-IGC") encoding the recombinant protein of the invention used in the Examples;

SEQ ID NO:30: amino acid sequence of the recombinant protein used in the Examples encoded by "3As-IGCD";

SEQ ID NO:31: DNA sequence ("3As-IGCD") encoding the recombinant protein of the invention used in the Examples;

SEQ ID NO:32: amino acid sequence of a VP1 epitope of bovine O serotype FMDV;

SEQ ID NO:33: amino acid sequence of a VP1 epitope of bovine O serotype FMDV;

SEQ ID NO:34: amino acid sequence of a VP1 epitope of bovine O serotype FMDV;

SEQ ID NO:35: cIGC 5' primer for amplifying the nucleotide sequence encoding the constant region of bovine immunoglobulin heavy chain;

SEQ ID NO:36: cIGC 3' primer for amplifying the nucleotide sequence encoding the constant region of bovine immunoglobulin heavy chain;

SEQ ID NO:37: amino acid sequence of the constant region of bovine immunoglobulin heavy chain;

SEQ ID NO:38: nucleotide sequence ("cIGC" fragment) encoding the constant region of bovine immunoglobulin heavy chain;

SEQ ID NO:39: amino acid sequence of the recombinant protein used in the Examples encoded by "3KO-cIGC";

SEQ ID NO:40: DNA sequence ("3KO-cIGC") encoding the recombinant protein of the invention used in the Examples;

SEQ ID NO:41: amino acid sequence of the recombinant protein used in the Examples encoded by "3KO-cIGCD";

SEQ ID NO:42: DNA sequence ("3KO-cIGCD") encoding the recombinant protein of the invention used in the Examples;

SEQ ID NO:43: amino acid sequence of residues 141-160 of the A serotype FMDV VP1 protein;

SEQ ID NO:44: amino acid sequence of residues 200-213 of the A serotype FMDV VP1 protein;

SEQ ID NO:45: amino acid sequence of the recombinant protein used in the Examples encoded by "3A-IGC";

SEQ ID NO:46: DNA sequence ("3A-IGC") encoding the recombinant protein of the invention used in the Examples;

SEQ ID NO:47: amino acid sequence of the recombinant protein used in the Examples encoded by "3A-IGCD"; and SEQ ID NO:48: DNA sequence ("3A-IGCD") encoding the recombinant protein of the invention used in the Examples.

DETAILED DESCRIPTION OF THE INVENTION

In one aspect, the present invention provides a vaccine composition for inducing a specific immune response against FMDV in an animal, which vaccine composition comprises a recombinant protein comprising from its N-terminus to C-terminus: a tandem repeat of an antigenic epitope of the FMDV capsid protein; the constant region of the immunoglobulin heavy chain or a functional fragment thereof; and the FMDV 3D protein or an immunogenic fragment thereof.

In a further aspect, the present invention provides a vaccine composition for inducing a specific immune response against FMDV in an animal, which vaccine composition comprises: (i) a recombinant protein comprising from its N-terminus to C-terminus: (a) a tandem repeat of an antigenic epitope of the FMDV capsid protein; and (b) the constant region of the immunoglobulin heavy chain or a functional fragment thereof; and (ii) the FMDV 3D protein or an immunogenic fragment thereof.

In a preferred embodiment of the vaccine composition of the invention, the antigenic epitope is derived from the FMDV capsid protein, such as an antigenic epitope derived from the FMDV VP1 protein.

In the anti-FMDV vaccine composition of the invention, an antigenic epitope of the FMDV VP1 protein useful in the construction of the recombinant protein can be a known major antigenic epitope of VP1 protein, for example, an epitope represented by amino acid residues 141-160 (SEQ ID NO:9) or amino acid residues 200-213 (SEQ ID NO:10) of porcine O serotype FMDV VP1 protein. It has been demonstrated that these epitopes can elicit B lymphocyte response in animals infected by FMDV.

To enhance the immunogenicity of the recombinant protein in the vaccine of the invention, the antigenic epitope of FMDV (e.g., an antigenic epitope of VP1 protein) is tandemly repeated in the recombinant protein constructed for use in the vaccine of the invention. In addition, the tandem repeat may be formed by one or more antigenic epitopes of FMDV (e.g., antigenic epitopes of VP1 protein) that are tandemly repeated. In this regard, the phrase "a tandem repeat of an antigenic epitope", as used herein, is intended to mean that, in the amino acid sequence of the recombinant protein, each of the antigenic epitopes (which can be either identical or different) is orderly linked directly, or indirectly via a linker, to another, and each of these tandemly linked antigenic epitopes (which can be either identical or different) is repeated for two or more times, for example, for three times. The phrase "a tandem repeat of an antigenic epitope", as used herein, also encompasses a plurality of different antigenic epitopes of FMDV (e.g., three epitopes) which are arranged in tandem and linked directly, or indirectly via a linker, to each other in the amino acid sequence of the recombinant protein, and wherein each of the epitopes may appear for one or more times (e.g., for 2 or 3 times).

In preferred embodiments of the vaccine composition of the invention, the antigenic epitope in the recombinant protein is repeated for 2 to 5 times in the tandem repeat. Repetitions of greater than 5 are also possible, but repetitions of less than 5 will make it more convenient to express the recombinant protein of the invention by means of recombinant expression. More preferably, the antigenic epitope in the recombinant protein is repeated for 3 times in the tandem repeat.

In a particular embodiment of the vaccine composition of the invention, the tandem repeat in the recombinant protein is a tandem repeat of two antigenic epitopes derived from the FMDV VP1 protein. In one particular embodiment, the tandem repeat is formed by two antigenic epitopes which are arranged in tandem and repeated for three times, wherein said two antigenic epitopes are respectively represented by the amino acid sequence of the residues 141-160 (SEQ ID NO:9) and the amino acid sequence of the residues 200-213 (SEQ ID NO:10) of porcine O serotype FMDV VP1 protein. As demonstrated in the experiment part, this recombinant protein can protect animals by effectively inducing a specific immune response against the O serotype FMDV in animal.

FIG. 1 illustrates the construction of the vaccine of the invention with reference to the anti-O serotype FMDV vaccine composition, in which the N-terminus of the recombinant protein is a region of the tandem repeat of an antigenic epitope of the O serotype FMDV VP1 protein, followed by the constant region of the immunoglobulin heavy chain of livestock origin, and the FMDV 3D protein can be either directly linked to the C-terminus of the constant region of the immunoglobulin heavy chain (FIG. 1A), or a separate protein component (FIG. 1B).

In a preferred embodiment of the vaccine of the invention, the antigenic epitopes and/or the tandem repeats in the recombinant protein are linked via a peptide linker to each other. The peptide linker between the antigenic epitopes and/or the tandem repeats should not influence the linear structure of the antigenic epitopes. Examples of the peptide linkers that can be used in the present invention are, for example, GGSSGG (SEQ ID NO:11), GGGSGGGS (SEQ ID NO:12), and GGGGS (SEQ ID NO:27). The experimental data provided herein show that the above "GS linkers" can be used as peptide linkers in the present invention which will not influence the linear structure of the antigenic epitopes arranged in the form of tandem repeat in the recombinant protein, and the recombinant protein can elicit the production of protective antibodies in the animal. In addition, in the recombinant protein in the vaccine of the invention, the tandem repeat of antigenic epitope(s) can also be linked to the amino acid sequence of the constant region of the immunoglobulin heavy chain via peptide linkers as mentioned above.

In order that the antigenic epitopes arranged in the form of tandem repeat can be displayed on the surface of the recombinant protein molecule, the antigenic epitopes, for example, the antigenic epitopes of VP1 protein, arranged in the form of tandem repeat are linked to the constant region of the immunoglobulin heavy chain or a functional fragment thereof. The constant region of the immunoglobulin heavy chain is capable of displaying the sequence of the variable region of antibody on the surface of the immunoglobulin molecule. By taking the advantage of this property of the constant region of the immunoglobulin heavy chain, the inventor replaces the variable region of the immunoglobulin heavy chain with the antigenic epitopes that are arranged in the form of tandem repeat, allowing the constant region of the immunoglobulin heavy chain to display the antigenic epitopes, for example, the tandem repeat of the antigenic epitopes of VP1 protein, on the surface of the recombinant protein molecule. Upon administering the vaccine of the invention into an animal, the B cell surface IgM monomers can contact with the antigenic epitope in the recombinant protein molecule and then be activated, leading to the production of immune response. The experiments conducted on animals confirm that the vaccine designed in this way can elicit robust protective immune response, which can achieve the purpose of protecting animals from infection.

Preferably, the constant region of the immunoglobulin heavy chain that can be used in the recombinant protein of the invention is of livestock origin. To reduce the immunogenicity of the constant region of the immunoglobulin heavy chain in the recombinant protein molecule, it is preferred to use a constant region of the immunoglobulin heavy chain which is from the same species as the animal to be vaccinated. The constant region of the immunoglobulin heavy chain can be derived from IgA, IgM, IgE, IgD, or IgG or a subtype of them. A "functional fragment" of the constant region of the immunoglobulin heavy chain refers to a portion of the constant region of the immunoglobulin heavy chain which retains the ability to display the tandem repeat of the antigenic epitopes on the surface of the recombinant protein molecule.

Another portion or component in the vaccine of the invention is the FMDV 3D protein or an immunogenic fragment thereof, preferably the intact 3D protein. The FMDV 3D protein and the antigenic epitopes from the capsid protein such as VP1 protein can be from the same type of FMDV. Alternatively, they can be from different types of FMDV. For example, in the vaccine of the invention, the antigenic epitopes of VP1 protein can be derived from the O serotype FMDV, while the 3D protein can be derived either from O serotype FMDV or from A serotype or Asia 1 FMDV.

In the vaccine of the invention, the FMDV 3D protein can be directly linked to the C-terminus of the constant region of the immunoglobulin heavy chain, so as to form an entire recombinant protein comprising the tandem repeat of antigenic epitopes of the FMDV VP1 protein, the constant region of the immunoglobulin heavy chain, and the FMDV 3D protein. Alternatively, the 3D protein can be present as a separate protein component which, together with the recombinant protein comprising the tandem repeat of antigenic epitopes of VP1 protein and the constant region of the immunoglobulin heavy chain, forms the effective components of the vaccine of the invention.

The purpose of introducing the FMDV 3D protein into the vaccine of the invention, either as a portion of the recombinant protein or as a separate component, is to elicit T cell response in the animal being vaccinated. T cells can attack the cells being infected by the virus in the animal body, and clean out the virus by eliminating the infected cells. Accordingly, T cell response plays a crucial role in protecting animals from virus infection. After animals being vaccinated with the vaccine of the invention, the antigen-presenting cells (APCs) can uptake and process the protein components in the vaccine, and the processed components can be presented on the surface of APCs by MHC molecules. This will induce the activation and proliferation of antigen-specific cytotoxic T lymphocytes, and the generation of immune memory cells. An "immunogenic fragment" of the FMDV 3D protein refers to a portion of the 3D protein which can also efficiently elicit T cell response in the animal being vaccinated as the intact 3D protein does.

In a particular embodiment of the vaccine of the invention, the N-terminus of the recombinant protein is formed by two antigenic epitopes of O serotype FMDV VP1 protein arranged in tandem and repeated for three times, in which the two antigenic epitopes are SEQ ID NO:9 (amino acid residues 141-160 of VP1) and SEQ ID NO:10 (amino acid residues 200-213 of VP1) which are linked by the peptide linker SEQ ID NO:11, and this tandem repeat is linked to the immunoglobulin heavy chain (SEQ ID NO:4) at its C-terminus by the peptide linker SEQ ID NO:11, and the C-terminus of the recombinant protein is formed by the intact 3D protein sequence of O serotype FMDV, thereby forming the entire recombinant protein (SEQ ID NO:8). In another particular embodiment, the N-terminus of the recombinant protein is formed by two antigenic epitopes of O serotype FMDV VP1 protein arranged in tandem and repeated for three times, in which the two antigenic epitopes are SEQ ID NO:9 (amino acid residues 141-160 of VP1) and SEQ ID NO:10 (amino acid residues 200-213 of VP1) which are linked by the peptide linker SEQ ID NO:11, and the C-terminus of the recombinant protein is formed by the immunoglobulin heavy chain (SEQ ID NO:4), and the above two portions are linked by the peptide linker SEQ ID NO:11, while the intact 3D protein is a separate independent component. As such, the recombinant protein (SEQ ID NO:13) component and the 3D protein (SEQ ID NO:6) component together form the effective components of the vaccine composition.

The present invention also encompasses the recombinant protein as described in the above aspects.

In a further aspect, the present invention provides an isolated polynucleotide encoding the recombinant protein in the vaccine composition of the invention.

The methods of obtaining the polynucleotide encoding the recombinant protein of the invention are known in the art. For example, the polynucleotide molecule can be directly prepared through chemical synthesis. Alternatively, it is possible to first obtain the nucleic acid molecules respectively encoding the tandem repeat of antigenic epitopes, the constant region of the immunoglobulin heavy chain or a functional fragment thereof, and the FMDV 3D protein or an immunogenic fragment thereof, add the sequence encoding the peptide linker, and then link them together to form the polynucleotide encoding the entire recombinant protein. For example, by RT-PCR amplification, it is possible to obtain the polynucleotide encoding the constant region of the immunoglobulin heavy chain from the spleen cells of an animal, and the polynucleotide encoding the 3D protein from an FMDV sample.

The polynucleotide of the invention can be used to prepare the components in the vaccine of the invention, for example, by inserting the polynucleotide into a suitable vector and then introducing it into a host cell to express the recombinant protein.

Accordingly, in a further aspect, the present invention provides a method of preparing a recombinant protein for use in a vaccine composition for inducing a specific immune response against FMDV in an animal, the method comprising the steps of:
  obtaining a polynucleotide encoding the recombinant protein as described above;
  constructing an expression vector containing the polynucleotide;
  introducing the expression vector into a host cell; and
  culturing the host cell under conditions suitable for the expression of the recombinant protein, recovering and purifying the expressed recombinant protein.

The expression vectors, for example, a prokaryotic or eukaryotic expression vector, that can be used to introduce the polynucleotide of the invention into a host cell are also known in the art.

The host cells that can be used to express the recombinant protein of the invention are, for example, *Escherichia coli* and yeast cells.

The anti-FMDV vaccine composition of the invention comprises an effective amount of the effective component(s), i.e., the entire recombinant protein or the recombinant protein component and the separate 3D component, together with a pharmaceutically acceptable carrier and adjuvant. The animals are cloven-hoofed animals, such as, pigs, cattles, or sheeps. As used herein, "an effective amount" means that the component or components of the vaccine are in an amount that is sufficient to induce a specific immune response against FMDV in the animal being vaccinated.

Suitable carrier and adjuvant are, for example, inorganic adjuvants, such as aluminium hydroxide or aluminium phosphate; organic adjuvants, such as CpG DNA or polyA; microorganisms and extracts thereof; and oil adjuvants, etc.

The present invention also provides a method of preventing FMDV infection in an animal comprising the step of administering to an animal in need thereof an effective amount of the vaccine composition of the invention. The vaccine of the invention can be administered in any route that is suitable for the administration of a protein vaccine, for example, by way of subcutaneous, intramuscular, intraperitoneal or intravenous injection. As used herein, "an effective amount" means that the component or components of the vaccine are in an amount that is sufficient to induce a specific immune response against FMDV in the animal being vaccinated. The effective amount can be readily determined by one skilled in the art, for example, through conventional experiments on animals. The protein components in the vaccine of the invention can be administered in a total amount of 100-2000 μg, preferably 200-1000 μg. Taking the recombinant protein in the Vaccine Composition A prepared in the Examples for an example, a single dosage administration of the recombinant protein in a amount of from 200 to 1000 μg can elicit an effective protective immune response against O serotype FMDV in the animal being vaccinated.

Methods and techniques for determining and evaluating the efficacy of the anti-FMDV vaccine composition are known in the art. Such methods and techniques include in vitro culture and titration of FMDV such as culture of hamster cells, in vitro propagation of virus, and preparation of protein; animal experiments such as collecting serum from the vaccinated animals, serum neutralization test, suckling mice protection test, $ID_{50}$ and $LD_{50}$ determination, and virus challenge tests in pigs; and immune response assays in animals, such as serum neutralizing antibody response assay and T cell response assay.

EXAMPLES

The following examples are presented only by way of illustration. The examples are not intended in any way to limit the scope of the invention.

Example 1

Construction of Recombinant Genes and Expression Vectors

Example 1a

Construction of O Serotype FMDV-Based Recombinant Gene and Expression Vector 1.1. Synthesis of the DNA Encoding the Tandemly Repeated Antigenic Epitopes of VP1 Protein The DNA encoding two antigenic epitopes of VP1 protein which are tandemly repeated for three times was obtained through DNA Synthesis. The two antigenic epitopes are from the O serotype FMDV causative of the recent outbreak of FMD, i.e., amino acid residues 141-160 (SEQ ID NO:9) and amino acid residues 200-213 (SEQ ID NO:10) of O serotype FMDV VP1 protein. The nucleotide sequence encoding a peptide linker (SEQ ID NO:11) was introduced between the nucleotide sequences encoding each of the tandemly repeated antigenic epitopes of VP1 protein. In addition, a methionine codon was added to the 5' end, and an additional nucleotide sequence encoding the peptide linker (SEQ ID NO:11) was added to the 3' end. The obtained product was designated as "3R" fragment, the nucleotide sequence of which is shown in SEQ ID NO:1.

1.2. Obtaining the Nucleotide Sequence Encoding the Constant Region of Porcine Immunoglobulin Heavy Chain The nucleic acid encoding the constant region of animal immunoglobulin heavy chain was obtained by RT-PCR amplification from animal spleen cells as outlined below. Total mRNA containing the mRNA for the constant region of heavy chain from porcine single chain IgG (scIgG) was extracted and purified from a pig spleen sample by using a FastPrep Kit (Gibco). The cDNA fragment encoding the scIgG was obtained by RT-PCR amplification by using the following primers (Kacskovics, I., Sun, J., Butler, J. E. Five putative subclasses of porcine IgG identified from the cDNA sequences of a single animal. J Immunol 1994; 153: 3565-73):

```
                                  SEQ ID NO: 15
scIgG 5' primer: 5'-GCCCCCAAGACGGCCCCA-3'

SEQ ID NO: 16
scIgG 3' primer: 5'-TCATCATTTACCCTGAGT-3'
```

M-MLV reverse transcriptase (Promega) was used for reverse transcription under the following conditions: 5 µl of M-MLV 5× reaction buffer (250 mM Tris-HCl (pH 8.3), 375 mM KCl, 15 mM MgCl$_2$, 50 mM DTT); 1.25 µl of each dNTP, 10 mM; 25 units of recombinant RNasin® RNase Inhibitor; 200 units of M-MLV reverse transcriptase; 2 µg mRNA; 0.5 µg of primers; adding RNase free water to a final volume of 25 µl. The reaction was conducted at 37° C. for 60 minutes, and then inactivated at 70° C. for 15 minutes.

The obtained product was then used as the template for subsequent PCR amplification. The total volume of the PCR amplification system was 25 µl, containing 2.5 µl of 10×PCR buffer (100 mM Tris-HCl, pH 8.4, 500 mM KCl, 1 mg/ml glutin), 0.5 µl of 10 mM dNTP, 0.5 µl of 50 mM MgCl$_2$, 1 µl of scIgG 5' primer (SEQ ID NO:15) (10 mM), 1 µl of scIgG 3' primer (SEQ ID NO:16) (10 mM), 0.2 µl of Taq polymerase (Promega), 1 µl of template, 18.3 µl of ddH$_2$O. The PCR was conducted under the following conditions: 95° C. for 5 minutes; 34 cycles of 95° C. for 30 seconds, 52° C. for 30 seconds, and 72° C. for 2 minutes; and finally, 72° C. for 5 minutes. The obtained amplification product was designated as "IGC" fragment. Sequencing analysis revealed that this fragment has the nucleotide sequence as shown in SEQ ID NO:3.

1.3. Ligation of the Nucleic Acids Encoding the Tandem Repeat Region and the Constant Region of Porcine Immunoglobulin Heavy Chain Ligation of the nucleic acid encoding the tandem repeat of antigenic epitopes of VP1 protein (3R fragment) and the cDNA for the constant region of porcine immunoglobulin heavy chain (IGC fragment) was conducted in a ligation reaction system containing: 300 mM Tris-HCl (pH 7.7), 100 mM MgCl$_2$, 50 mM DTT and 1 mM ATP. The molar ratio of the nucleic acid encoding the tandem repeat of antigenic epitopes of VP1 protein to the cDNA fragment for the constant region of heavy chain was 1:1.2 u T4 DNA ligase and 0.2 u T4 RNA ligase (Promega) were used to enhance the efficiency of the ligation. The ligation product was designated as "3R-IGC" fragment, the nucleotide sequence of which is shown in SEQ ID NO:14.

1.4. Obtaining the Nucleic Acid Encoding the FMDV 3D Protein

The following primers were used for cloning the nucleic acid encoding the FMDV 3D protein from a blister fluid sample obtained from a pig infected by O serotype FMDV:

```
3D 5' primer:
                                     SEQ ID NO: 17
5'-CCATCTCCAAGACTCAGGGTAAAGGGTTGATCGTCGACACC-3'

3D 3' primer:
                                     SEQ ID NO: 18
5'-GTATGCGTCACCGCAC-3'
```

The RT-PCR conditions were same as that used in amplification of IGC. The product amplified from FMDV was designated as "D" fragment. This product encodes the FMDV 3D protein and has the nucleotide sequence as shown in SEQ ID NO:5.

1.5. Obtaining the Nucleic Acid Encoding the Entire Recombinant Protein

The "3R-IGC" fragment as prepared above was then ligated with the "D" fragment encoding the 3D protein amplified from FMDV by overlapping PCR, thereby obtaining the nucleic acid molecule "3R-IGCD" encoding the entire recombinant protein. The detailed steps are as follows.

(1) Designing the primers for "3R-IGC" fragment amplification:

```
3R-IGCD 5' primer:
                                     SEQ ID NO: 19
5'-AGCTGAATTCATGGTACCAAACCTG-3'

3R-IGC 3' primer1:
                                     SEQ ID NO: 20
5'-GGTAGAGGTTCTGAGTCCCATTTCCCAACTAGCAGCTGTGG-3'
```

The 3R-IGCD 5' primer is complementary to the 5' end of the "3R-IGC" fragment, and the 3R-IGC 3' primer 1 is partially complementary to the 3' end of the "3R-IGC" fragment and partially complementary to the 5' end of the "D" fragment. The PCR amplification produced the 3R-IGC portion of the 3R-IGCD, the 3' end sequence of which is partially identical to the 5' end of the "D" fragment.

(2) Designing the primers for "D" fragment amplification:

```
D 5' primer:
                                     SEQ ID NO: 21
5'-CCATCTCCAAGACTCAGGGTAAAGGGTTGATCGTCGACACC-3'

3R-IGCD 3' primer:
                                     SEQ ID NO: 22
5'-AGCTTCTAGAAATTTATGCGTCACCGCAC-3'
```

The D 5' primer is partially complementary to the 5' end of the "D" fragment and partially complementary to the 3' end of the "3R-IGC" fragment, and the 3R-IGCD 3' primer is complementary to the 3' end of the "D" fragment. The PCR amplification produced the D portion of the 3R-IGCD, the 5' end sequence of which is partially identical to the 3' end of the "3R-IGC" fragment.

(3) 5 µg of each of the 3R-IGC portion and the D portion were used as the PCR primers and template for each other, subjected to 6 cycles of 95° C. denature for 1 minute, 65° C. elongation for 2 minutes. And then, the 3R-IGCD 5' primer and the 3R-IGCD 3' primer were added to this reaction system, subjected to 20 cycles of 95° C. denature for 1 minute, 55° C. 30 seconds, 72° C. elongation for 2 minutes. The obtained amplification product is the 3R-IGCD (SEQ ID NO:7), encoding the recombinant protein in the Vaccine Composition A as prepared in Example 2.

1.6. Construction of Expression Vector

The amplification product "3R-IGCD" obtained as described above was digested with EcoR I and Xba I and then inserted into the bacterial expression vector pET22b (Novagen Inc.), thereby obtaining the plasmid p3R-IGCD.

The following primers were used in PCR amplification of the "3R-IGC" prepared in above Section 1.3:

```
3R-IGC 5' primer:
                                     SEQ ID NO: 23
5'-AGCTGAATTCATGGTACCAAAC-3'

3R-IGC 3' primer2:
                                     SEQ ID NO: 24
5'-AGCTTCTAGATCATCATTTACCCTGAGT-3'
```

The amplification product was digested with EcoR I and Xba I and then inserted into the bacterial expression vector pET22b (Novagen Inc.), thereby obtaining the plasmid p3R-IGC.

Example 1b

Construction of Asia 1 FMDV-Based Recombinant Gene and Expression Vector

The DNA encoding the tandemly repeated antigenic epitopes of Asia 1 FMDV VP1 protein was synthesized in a way similar to that described in Section 1.1 of Example 1a. In brief, the DNA encoding two antigenic epitopes of Asia 1 FMDV VP1 protein which are tandemly repeated was obtained through DNA synthesis. The two antigenic epitopes respectively have the amino acid sequence of residues 133-158 (SEQ ID NO:25) and amino acid sequence of residues 200-213 (SEQ ID NO:26) of Asia 1 FMDV VP1 protein. The nucleotide sequence encoding a peptide linker (SEQ ID NO:11) was introduced between the nucleotide sequences encoding each of the tandemly repeated antigenic epitopes of VP1 protein. In addition, a methionine codon was added to the 5' end of the DNA sequence, and an additional nucleotide sequence encoding a peptide linker (SEQ ID NO:27) was added to the 3' end. The obtained product was designated as "3As" fragment.

The 3As was ligated with the IGC (SEQ ID NO:3) as obtained in Section 1.2 of Example 1a in a way similar to that described in Section 1.3 of Example 1a. The ligation product was designated as "3As-IGC" fragment, having the nucleotide sequence as shown in SEQ ID NO:29, and the amino acid sequence encoded by "3As-IGC" is shown in SEQ ID NO:28.

The "3As-IGC" fragment was then ligated with the "D" fragment (SEQ ID NO:5) obtained in above Section 1.4 by way of overlapping PCR similar to that described in Section 1.5 of Example 1a, thereby obtaining the nucleic acid molecule "3As-IGCD" encoding the entire Asia 1 FMDV-based recombinant protein. Sequencing analysis revealed that it has the DNA sequence as shown in SEQ ID NO:31, and the encoded amino acid sequence is SEQ ID NO:30.

Finally, the "3As-IGCD" was digested with EcoR I and Xba I and then inserted into the bacterial expression vector pET22b (Novagen Inc.), obtaining the plasmid p3As-IGCD.

Example 1c

Construction of Bovine O Serotype FMDV-Based Recombinant Gene and Expression Vector The DNA encoding the tandemly repeated antigenic epitopes of bovine O serotype FMDV VP1 protein was synthesized in a way similar to that described in Section 1.1 of Example 1a. In brief, the DNA encoding three antigenic epitopes of bovine O serotype FMDV VP1 protein which are tandemly repeated was obtained through DNA synthesis. The antigenic epitopes of VP1 protein respectively have the amino acid sequence of SEQ ID NO:32, SEQ ID NO:33, and SEQ ID NO:34. The nucleotide sequence encoding a peptide linker (SEQ ID NO:11) was introduced between the nucleotide sequences encoding each of the tandemly repeated antigenic epitopes of VP1 protein. In addition, a methionine codon was added to the 5' end of the DNA sequence, and an additional nucleotide sequence encoding a peptide linker (SEQ ID NO:27) was added to the 3' end. The obtained product was designated as "3KO" fragment.

The nucleotide sequence encoding the constant region of bovine immunoglobulin heavy chain was obtained in a way similar to that described in Section 1.2 of Example 1a. The following primers were used:

```
cIGC 5' primer:
                                      SEQ ID NO: 35
5'-CATGAAGCTTGCCTCCACCACAGCCCCGAAAG-3' cIGC 3' primer:
                                      SEQ ID NO: 36
5'-CCGGCTCGAGTTTACCCGCAGACTTAGAGGTGGACTTC-3'
```

Sequencing analysis revealed that the obtained cDNA, designated as "cIGC" fragment, has the sequence as shown in SEQ ID NO:38, and the encoded amino acid sequence is SEQ ID NO:37.

The 3KO was ligated with the cIGC in a way similar to that described in Section 1.3 of Example 1a. The ligation product was designated as "3KO-cIGC" fragment, having the nucleotide sequence as shown in SEQ ID NO:40, and the amino acid sequence encoded by "3KO-cIGC" is shown in SEQ ID NO:39.

The "3KO-cIGC" fragment was then ligated with the "D" fragment (SEQ ID NO:5) obtained in above Section 1.4 by way of overlapping PCR similar to that described in Section 1.5 of Example 1a, thereby obtaining the nucleic acid molecule "3KO-cIGCD" encoding the entire bovine O serotype FMDV-based recombinant protein. Sequencing analysis revealed that it has the DNA sequence as shown in SEQ ID NO:42, and the encoded amino acid sequence is SEQ ID NO:41.

Finally, the "3KO-cIGCD" was digested with EcoR I and Xba I and then inserted into the bacterial expression vector pET22b (Novagen Inc.), obtaining the plasmid p3KO-cIGCD.

Example 1d

Construction of A Serotype FMDV-Based Recombinant Gene and Expression Vector

The DNA encoding the tandemly repeated antigenic epitopes of A serotype FMDV VP1 protein was synthesized in a way similar to that described in Section 1.1 of Example 1a. In brief, the DNA encoding two antigenic epitopes of A serotype FMDV VP1 protein which are tandemly repeated was obtained through DNA synthesis. The two antigenic epitopes respectively have the amino acid sequence of residues 141-160 (SEQ ID NO:43) and amino acid sequence of residues 200-213 (SEQ ID NO:44) of A serotype FMDV VP1 protein. The nucleotide sequence encoding a peptide linker (SEQ ID NO:11) was introduced between the nucleotide sequences encoding each of the tandemly repeated antigenic epitopes of VP1 protein. In addition, a methionine codon was added to the 5' end of the DNA sequence, and an additional nucleotide sequence encoding a peptide linker (SEQ ID NO:27) was added to the 3' end. This linker is used for linking the tandemly repeated antigenic epitopes with the fragment of the constant region of porcine immunoglobulin heavy chain. The obtained product was designated as "3A" fragment.

The 3A was ligated with the IGC (SEQ ID NO:3) as obtained in Section 1.2 of Example 1a in a way similar to that described in Section 1.3 of Example 1a. The ligation product was designated as "3A-IGC" fragment, having the nucleotide sequence as shown in SEQ ID NO:46, and the amino acid sequence encoded by "3A-IGC" is shown in SEQ ID NO:45.

The "3A-IGC" fragment was then ligated with the "D" fragment (SEQ ID NO:5) obtained in above Section 1.4 by way of overlapping PCR similar to that described in Section 1.5 of Example 1a, thereby obtaining the nucleic acid molecule "3A-IGCD encoding the entire A serotype FMDV-based recombinant protein. Sequencing analysis revealed that it has the DNA sequence as shown in SEQ ID NO:48, and the encoded amino acid sequence is SEQ ID NO:47.

Finally, the "3A-IGCD" was digested with EcoR I and Xba I and then inserted into the bacterial expression vector pET22b (Novagen Inc.), obtaining the plasmid p3A-IGCD.

Example 2

Preparation of Vaccine 2.1. Preparation of Vaccine Composition A of the Invention 2.1.1. Expression of the Recombinant Protein Encoded by 3R-IGCD.

The competent cells (*E. coli*, BL21) were thawed on ice, and 300 µl of competent cells were added to each ice-cold tube. The plasmid p3R-IGCD as prepared in Example 1 was added to each tube, mixed and allowed to stand on ice for 40 minutes, and then subjected to heat shock in water bath at 42° C. for 45 seconds. 1 ml of L-culture medium (no antibiotics) was added to each tube. The tubes were incubated on a shaker at 37° C. for 45 minutes to allow the expression of protein from the plasmid. The transformed bacteria were plated on culture plate with ampicillin, and allowed to stay overnight at 37° C. The bacteria clones with ampicillin resistance were selected, and subjected to DNA sequencing after plasmid extraction. Strains containing the plasmids with correct sequence were then selected. The strains were inoculated in LB culture medium, and allowed to grow until OD=0.5 at 37° C., and then 0.4 mM IPTG was added to the culture so as to induce the expression of the recombinant protein. After 4 hours, the bacterial cells were collected. The suspension of bacterial cells was sonicated, and then centrifuged at 10,000×g for 10 minutes at 4° C., so as to remove residual bacterial debris. The supernatant was directly used for immunoblotting analysis. The insoluble protein (inclusion body) was collected by centrifugation at 30,000×g, and washed with LB culture medium once, then mixed with buffer 1 (SB1: 100 mM NaH$_2$PO$_4$, 10 mM Tris-HCl, 20 mM imidazole, pH 8.0, 1 mM DTT, 8 M urea, 1.5 M NaCl) in the amount of 25 ml per gram of precipitate with shaking, and incubated at room temperature for 20-30 minutes. The vitric insoluble cell wall was removed by centrifugation at 65,000×g for 30 minutes. The supernatant was filtrated through 0.2 µm filtration membrane, thereby obtaining the protein sample containing the recombinant protein. The expressed recombinant protein was purified with His-Trap column (Porath, J., Carlsson, J., Olsson, I., Belfrage, G Metal chelate affinity chromatography, a new approach to protein fraction. Nature 1975; 258: 598-99). 5-10 mg/ml of the above protein sample was placed on a 1×5 cm pre-equilibrated His-Trap column. The recombinant protein expressed from p3R-IGCD plasmid has a His-tail. The bound protein was washed with 50 ml SB1, and then was eluted from the column using elution buffer 2 (EB2: SB1+0.5 M NaCl+480 mM imidazole, pH 8.0). The eluted protein was 10-fold diluted with SB1, then subjected to a second chromatography under the same condition. The eluted proteins were combined, and the concentration thereof was determined using Bio-Rad protein analysis kit according to manufacturer's instruction. The concentration of the protein was adjusted to 0.3-0.4 mg/ml. Dialysis was performed with 5 L 50 mM Tris, pH 7.5, 1.0 M NaCl for 72 hours, with the dialysate being changed frequently. The protein was also purified using a similar method except that 6 M urea was used to dissolve protein instead of 8 M urea. The purified protein was stored at 4° C.

2.1.2. SDS-PAGE and Immunoblotting Analysis of the Recombinant Protein Encoded by 3R-IGCD.

Figures 2, 3:
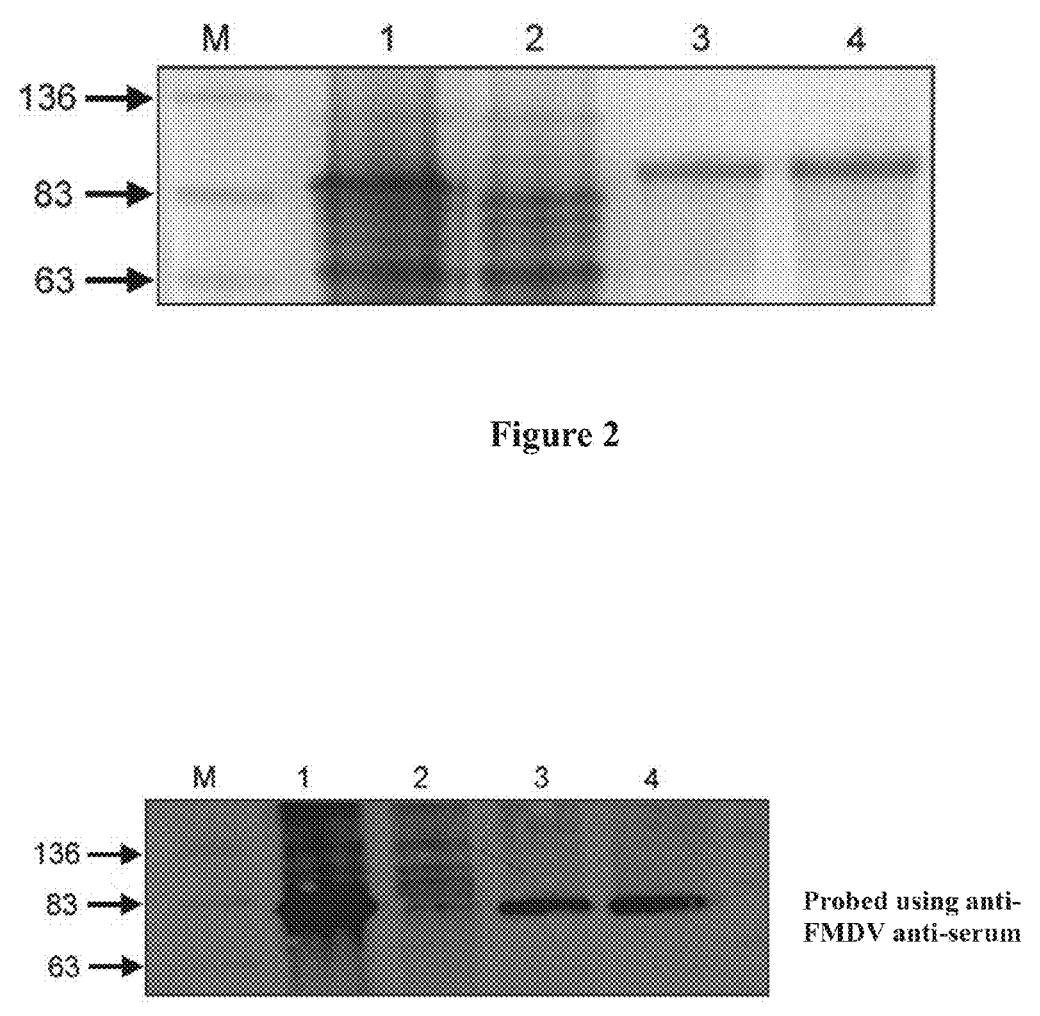

The expression of recombinant protein was revealed by SDS-PAGE gel electrophoresis. The result of SDS-PAGE showed that the molecular weight of the resulting recombinant protein was consistent with that as expected (FIG. 2). The expression of target protein was determined by immunoblotting (Amersham ECL immunoblotting kit) (Gel electrophoresis of proteins (Hammes, B. D., Rickwood, D., eds.), IRL Press, Oxford, 1981). In immunoblotting analysis, the anti-FMDV anti-sera obtained from pigs infected with O serotype FMDV were used (FIG. 3), and the results confirm that the recombinant protein is immunogenic and reactive with above sera.

2.1.3. Obtaining Vaccine Composition A.

Emulsifying agent 206 (SEPPIC Inc, France) was added to and mixed with the recombinant protein, thus obtaining the Vaccine Composition A of the invention (containing the 3R-IGCD-encoded recombinant protein (SEQ ID NO:8) as active ingredient).

2.2. Preparation of Vaccine Composition B of the Invention

According to the similar procedures as in Section 2.1, the plasmid p3R-IGC was used to express and purify the recombinant protein (having the amino acid sequence as shown in SEQ ID NO:13) encoded by 3R-IGC. The results from the Coomassie blue staining and immunoblotting assay (probed with anti-FMDV sera from pigs) of the SDS-PAGE of this recombinant protein were shown in FIG. 4.

Figure 5:
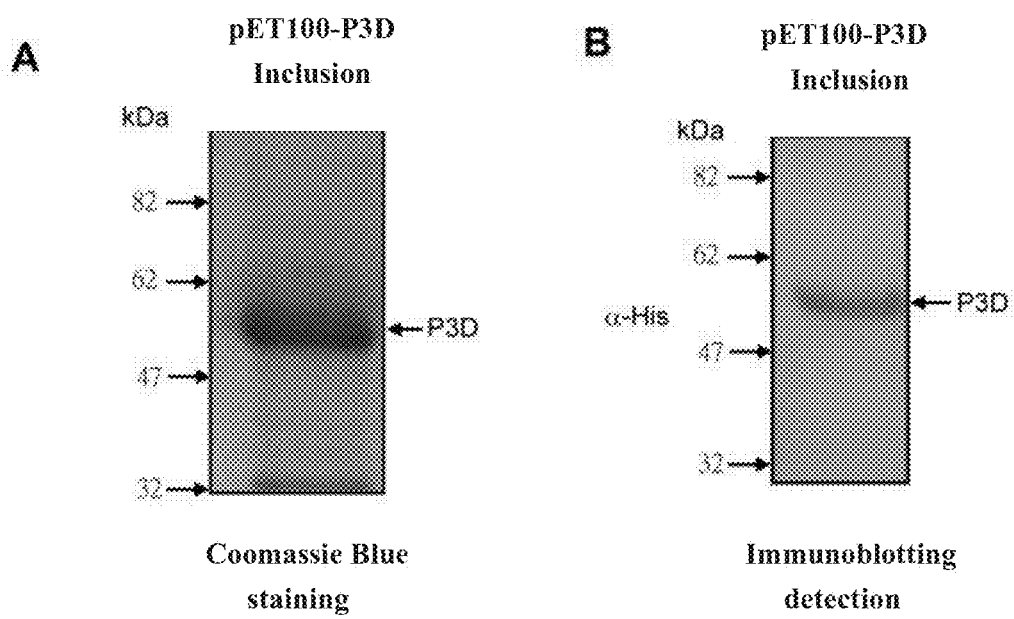
FIG. 5 shows the Coomassie blue staining and immunoblotting detection of the 3D protein component in the Vaccine Composition B of the invention.

The nucleic acid encoding the 3D protein of FMDV as obtained in Section 1.4 of Example 1 was cloned into expression vector pET100-D-TOPO (Invitrogen), thereby obtaining plasmid pET100-P3D. The vector pET100-D-TOPO has been linearized by the manufacturer, which can be linked to target fragment for the expression of the recombinant protein in bacteria. According to the similar procedures as in Section 2.1.1, the plasmid pET100-P3D was used to transform *E. coli*. strain BL21 codon plus. The cultured bacteria were induced with 0.4 mM IPTG for 4 hours, so as to express the 3D protein. The expressed and purified 3D protein was subjected to SDS-PAGE and Coomassie blue staining, and immunoblotting using anti-His antibody. The results were shown in FIG. 5.

The recombinant protein encoded by 3R-IGC and the 3D protein were mixed at equivalent molar ratio, to which emulsifying agent 206 (SEPPIC Inc, France) was added, thereby obtaining the Vaccine Composition B of the invention (containing 3R-IGC-encoded recombinant protein (SEQ ID NO:13) and the 3D protein (SEQ ID NO:6) as active ingredients).

2.3. Preparation of Other Vaccine Compositions of the Invention

The vaccines were prepared containing the recombinant proteins as generated in Example 1b, 1c and 1d using the similar procedures as in Sections 2.1 and 2.2, respectively. Said vaccines contain the entire recombinant protein "3As-IGCD", "3KO-cIGCD", or "3A-IGCD" as active ingredients, or contain the separate 3D component together with the recombinant protein "3As-IGC", "3KO-cIGC", or "3A-IGC" as active ingredients, respectively.

Example 3

Efficacy of the Anti-FMDV Vaccine

3.1. Cell Culture

Hamster Kidney Cell line (BHK21) (purchased from ATCC, ATCC CCL-10) was cultured in Essential Medium supplemented with 10% heat inactivated fetal bovine serum (FBS) (Gibco), penicillin (100 U ml$^{-1}$), streptomycin (100 μg ml$^{-1}$) and Earle salts, at 37° C. and 5% $CO_2$ (Barnett, P. V., L. Pullen, R. E Staple, L. J. Lee, R. Butcher, D. Parkinson, and T. R. Doel. 1996. A protective anti-peptide antibody against the immunodominant site of the $A_{24}$ Cruzeiro strain of foot-and-mouth disease virus and its reactivity with other subtype viruses containing the same minimum binding sequence. J. Gen. Virol. 77: 1011-1018).

3.2. FMDV Propagation and Preparation of Viral Protein

FMDV was derived from the epithelial tissue of blisters of pigs infected with FMDV upon prevalence. When BHK21 single layer cells grew to 80% confluence, 1 ml FMDV liquid was added to the surface of cell layer to propagate FMDV. The BHK21 cells were cultured at 37° C. for 45 minutes, and were harvested until cells exhibited 75% of cellular cytopathic effect, and then 20 ml essential medium (EMEM) supplemented with Earle salts and free from FBS were added. After culturing, 0.01 M Binary ethylenimine (Sigma) was added and the culture was placed at 37° C. for 1 hour to inactivate FMDV; then 7% polyethylene glycol (PEG 6000) (Sigma) was added and placed at 4° C. overnight to precipitate the inactivated FMDV. The total protein of virus was obtained by ultra-centrifugation at 40,000 rpm for 2 hours. The concentration of the purified viral protein was determined by measuring optical density at 259 nm (1 OD=132 μg) (Barnett, P. V., L. Pullen, R. F. Staple, L. J. Lee, R. Butcher, D. Parkinson, and T. R. Doel. 1996. A protective anti-peptide antibody against the immunodominant site of the $A_{24}$ Cruzeiro strain of foot-and-mouth disease virus and its reactivity with other subtype viruses containing the same minimum binding sequence. J. Gen. Virol. 77: 1011-1018). The viral protein was used for T cell proliferation assay.

3.3. Determination of the 50% Infective Dosage ($ID_{50}$) of FMDV

To determine the concentration of 50% Infective dosage ($ID_{50}$) of FMDV, 25 pigs negative for FMDV serum reaction were used for the analysis of 50% Infective dosage ($ID_{50}$). The animals were divided into 5 groups, 5 animals per group. The Foot-and-mouth disease virus liquid was 1:10 serially diluted (e.g., $10^{-4}$, $10^{-5}$, $10^{-6}$, $10^{-7}$ and $10^{-8}$), and injected to the cervical muscle of pigs, respectively. 2-10 days after virus challenge, observation was made to the nasal, buccal, glossal and podalic blister formation, with body temperature being recorded everyday. The pigs with FMD symptoms and a body temperature above 40° C. were identified as FMD positive. The diluted concentration at which 50% pigs exhibited positive symptoms due to FMDV infection was defined as $ID_{50}$ of FMDV liquid, ie. 1 $ID_{50}$ (Collen, T., R. Dimarchi, and T. R. Doel. 1991. A T Cell Epitope in VP1 of Foot-and-Mouth Disease Virus is Immunodominant for Vaccinated Cattle. J. Immunol. 14G: 749-755. Taboga, O., C. Tami, E. Carrillo, J. I. Nunez, A. Rodriguez, J. C. Saiz, E. Blanco, M. L. Valero, X. Roig, J. A. Camarero, D. Andreu, M. G Mateu, E. Giralt, E. Domingo, E Sobrino, and E. L. Palma. 1997. A Large-Scale Evaluation of Peptide Vaccines against Foot-and-Mouth Disease: Lack of Solid Protection in Cattle and Isolation of Escape Mutants. J. Virol. 71: 2604-2614).

3.4. Serum Collection and Virus Challenge Test of Vaccinated Pigs

FMDV virus challenge test is a method to determine the efficiency of recombinant vaccine. Totally 25 pigs (2.5 month old, about 25 kg) negative for FMDV serum reaction were used for virus challenge analysis.

The pigs were divided into 5 groups: (a) 5 were used as negative control (injected with 1 ml PBS); (b) 5 were used as positive control (injected with 2 ml commercial FMD vaccine (Inactivated whole virus), China Agricultural VET. BIO. Science and Technology Co. LTD., Lanzhou, China, following the dosage recommended by the manufacturer); the reaming groups c, d, e were injected with Vaccine Composition A, ie., the recombinant protein (encoded by "3R-IGCD") as prepared in Section 2.1 of Example 2, as follows: (c) 5 were injected with 0.2 mg of the recombinant protein; (d) 5 were injected with 0.5 mg of the recombinant protein; (e) 5 were injected with 1 mg of the recombinant protein. When testing the Vaccine Composition B as prepared in Section 2.2 of Example 2, grouping was the same as above for testing Vaccine Composition A, the total amount of protein injected was the same as Vaccine Composition A, wherein the molar ratio of the recombinant protein (encode by "3R-IGC") to the 3D protein was 1:1.

At the beginning, the pigs were vaccinated at the cervical muscle for the first time, and then vaccinated again at the same dosage on day 21. Serum samples were collected on day 0 and day 51 from animals of each group and tested. One week later, the animals were challenged with FMDV at 1000× $ID_{50}$, and the diagnostic criteria for identifying FMD were the same as those in above $ID_{50}$ determination (Rodriguez, A., J. C. Salz, I. S, Novella, D. Andreu, and E Sobrino. 1994. Antigenic Specificity of Porcine T Cell Response against Foot-and-Mouth Disease Virus Structural Proteins: Identification of T Helper Epitopes in VP1. Virology 205: 24-33).

3.5. Serum Antibody Neutralization Test (SNT)

For the five groups of pigs that were injected respectively with the recombinant protein, the commercial anti-FMD vaccine, and the buffer, in order to determine their specific antibody response to FMDV, Serum Neutralization Tests (SNT) were performed according to the procedure prescribed by the World Reference Laboratory for FMD (Chapter 2.1.1 Foot and mouth disease. In: "OIE Manual". Office International des Epizooties, Paris, 1996; 47-56.). The concentrations of antibodies are represented in the form of $\log_{10} SN_{50}$ (Salt, J. S., P. V. Barnett, P. Dani, and L. William. 1998. Emergency vaccination of pigs against foot-and-mouth disease: protection against disease and reduction in contact transmission. Vaccine 16: 746-754). The results are shown in Tables 1 and 2.

TABLE 1

Antibody neutralization reactions: pigs were vaccinated with 200 μg, 500 μg and 1 mg of the recombinant protein (Vaccine Composition A), the buffer and the commercial anti-FMD vaccine, respectively, and antibody neutralization reactions were conducted on day 51 of vaccination.

| Samples tested | Dose of protein (μg) | Titers of neutralizing antibodies ($\log_{10}SN_{50}$)[a] |
|---|---|---|
| Vaccine Composition A | 200 | 1.55 ± 0.64 |
|  | 500 | 1.76 ± 0.21 |
|  | 1000 | 1.82 ± 0.25 |
| Buffer[b] |  | <0.4 |
| Commercial anti-FMD vaccine[b] |  | 2.36 ± 0.43 |

[a]The average titers of neutralizing antibodies from five pigs ± SEM (the standard error of the mean);
[b]The commercial anti-FMD vaccine: positive control; the buffer: negative control.

TABLE 2

Antibody neutralization reactions: pigs were vaccinated with 200 µg, 500 µg and 1 mg of the recombinant protein (Vaccine Composition B, in which the molar ratio of the recombinant protein to 3D protein is 1:1), the buffer and the commercial anti-FMD vaccine, respectively, and antibody neutralization reactions were conducted on day 51 of vaccination.

| Samples tested | Dose of protein (µg) | Titers of neutralizing antibodies ($\log_{10}SN_{50}$)[a] |
|---|---|---|
| Vaccine Composition B | 200 | 1.45 ± 0.80 |
|  | 500 | 1.64 ± 0.32 |
|  | 1000 | 1.84 ± 0.37 |
| Buffer[b] |  | <0.4 |
| Commercial anti-FMD vaccine[b] |  | 3.55 ± 0.63 |

[a]The average titers of neutralizing antibodies from five pigs ± SEM (the standard error of the mean);
[b]The commercial anti-FMD vaccine: positive control; the buffer: negative control.

The results of Serum Neutralization Tests show that, after vaccination with Vaccine Composition A or Vaccine Composition B (200 µg, 500 µg and 1 mg), antibody neutralization reaction against FMDV can be elicited in all the pigs that were previously negative in FMDV serum reaction (Tables 1 and 2). The pigs in the negative control group were not vaccinated with the recombinant protein or the commercial anti-FMD vaccine, and thus no antibody reaction was detected. There is no statistically significant difference between the antibody levels of the three groups vaccinated with our vaccine and the group vaccinated with commercial anti-FMD vaccine.

3.6. Suckling Mouse Protection Test

Suckling mouse protection test (MPT) is the second method to determine whether the pigs vaccinated with the vaccine of the present invention can produce antibodies against FMDV. The mouse protection test was performed as described in Mulcahy et al. with modification (Mulcahy, G., L. A. Pullen, C. Gale, R. D. DiMarchi, and T. R. Doel. 1991. Mouse protection test as a predictor of the protective capacity of synthetic foot-and-mouth disease vaccines. Vaccine 9:19-24). The 50% Lethal Dose ($LD_{50}$) of the FMDV material: 5 virus samples diluted by serial dilutions (such as $10^{-3}$, $10^{-4}$, $10^{-5}$, $10^{-6}$ and $10^{-7}$) were injected into 5 groups of suckling mice (4 mice in each group), the diluted concentration which causes 50% death in the mice was then determined as the $LD_{50}$. The anti-sera of the experimental pigs (vaccinated with the vaccine of the invention (Vaccine Composition A or Vaccine Composition B), the commercial anti-FMD vaccine, and the buffer, respectively) were taken on the day 51 of vaccination. All the anti-sera were inactivated at 56° C. for 30 minutes. Four 3-4 day old suckling mice in each group were intraperitoneally injected (i.p.) with 100 µl undiluted pig antiserum, respectively. Within 20-23 hours, all the mice were respectively challenged by FMDV at a dose of 10, 100, or 1000 times of the 50% Lethal Dose ($LD_{50}$), and were then observed for 4 days. The number of mice that remained alive was recorded. The results are shown in Table 3.

TABLE 3

Suckling mouse protection test: suckling mice protected by the anti-sera taken from the pigs on day 51 of vaccination with 200 µg, 500 µg and 1 mg of the vaccine of the invention (Vaccine Composition A or Vaccine Composition B), the buffer, and the commercial anti-FMD vaccine.

| Samples tested | Dose of the protein (µg) | Percentage of the mice protected[a] | | |
|---|---|---|---|---|
|  |  | 1000 $LD_{50}$ | 100 $LD_{50}$ | 10 $LD_{50}$ |
| Vaccine Composition A/Vaccine Composition B | 200 | 100/100[b] | 100/100 | 100/100 |
|  | 500 | 100/100 | 100/100 | 100/100 |
|  | 1000 | 100/100 | 100/100 | 100/100 |
| Commercial anti-FMD vaccine |  | 100/100 | 100/100 | 100/100 |
| Buffer |  | 0 | 0 | 0 |

[a]Each valve represents the average degree of protection of the suckling mice (4 in each group) in every group;
[b]Before the "/" is the percentage of protection produced by Vaccine Composition A, and after the "/" is the percentage of protection produced by Vaccine Composition B.

It is clearly shown in Table 3 that, the anti-sera from the pigs that were vaccinated with either 200 µg, 500 µg or 1 mg of Vaccine Composition A or Vaccine Composition B all can completely protect the suckling mice against the challenge of FMDV at a dose of 1000 times of the 50% Lethal Dose ($LD_{50}$). The anti-sera of the pigs that were not vaccinated with the recombinant protein (the negative control group) were totally unable to protect the suckling mice against the infection of FMDV; while the anti-sera of the pigs that were vaccinated with the commercial anti-FMD vaccine can protect the suckling mice against the challenge of FMDV at a dose up to 1000 times of the 50% Lethal Dose ($LD_{50}$).

3.7. T-Cell Proliferation Analysis

T-cell proliferation analysis was performed to characterize the T-cell proliferation caused by the injection of the recombinant protein. T-cells were collected from the groups of pigs that were vaccinated with Vaccine Composition A or Vaccine Composition B, the commercial anti-FMD vaccine, and the buffer. The blood cells were purified through 1.077 g ml$^{-1}$ of Percoll solution. $4 \times 10^6$ T-cells/ml for each group were cultured in 96-well plate (Corning), and FMDV viral protein was added to a concentration of 10 µg ml$^{-1}$ or 50 µg ml$^{-1}$. The plate was cultured at 37° C. for 4 days and then 1 microcurie (µCi) per 25 µl of [tritium]thymidine ([$^{3H}$]thymidine) was added, the cells were collected after culturing for 18 hours and measured using liquid scintillation counter (Beckman LS6500) (Measurement of proliferation Response of Cultured lymphocytes, Chapter 7.10, Current Protocols in Immunology, Edited by J. E. Cologan (NIH), 2005, Johm Wiley and Sons, Inc. Lierop, M. J. C. V., K. V. Maanen, R. H. Meloen, V. P. M. G Rutten, M. A. C. Dejong, and E. J. Hensen. 1992. Proliferative Lymphocyte responses to foot-and-mouth disease virus and three FMDV peptides after vaccination or immunization with these peptides in cattle. Immunol. 75: 406-413).

TABLE 4

T-cell Response in pigs received two vaccinations of Vaccine Composition A to FMDV protein.

| Immunogen | Pig No. | First vaccination | | Second vaccination | |
|---|---|---|---|---|---|
|  |  | T-cell Stimulation Index (S.I.[b]) | | | |
|  |  | 10 µg/ml | 50 µg/ml | 10 µg/ml | 50 µg/ml |
| Vaccine Composition A 0.2 mg | 1 | 1.5 | 2.1 | 3.2 | 9.0 |
|  | 2 | 1.4 | 2.3 | 2.8 | 7.9 |
|  | 3 | 1.6 | 1.9 | 2.9 | 6.7 |

TABLE 4-continued

T-cell Response in pigs received two vaccinations
of Vaccine Composition A to FMDV protein.

| Immunogen | Pig No. | First vaccination T-cell Stimulation Index (S.I.[b]) | | Second vaccination T-cell Stimulation Index (S.I.[b]) | |
|---|---|---|---|---|---|
| | | 10 μg/ml | 50 μg/ml | 10 μg/ml | 50 μg/ml |
| Vaccine | 1 | 1.6 | 1.9 | 2.9 | 8.0 |
| Composition A | 2 | 1.2 | 2.1 | 3.5 | 7.7 |
| 0.5 mg | 3 | 1.4 | 1.9 | 3.4 | 6.5 |
| Vaccine | 1 | 1.3 | 2.0 | 3.4 | 8.1 |
| Composition A | 2 | 1.7 | 1.8 | 3.3 | 9.7 |
| 1 mg | 3 | 1.7 | 1.8 | 2.9 | 8.8 |
| Positive | 1 | 1.8 | 2.1. | 4.4 | 8.5 |
| control group | 2 | 1.3. | 1.9 | 2.7 | 9.7 |
| (Commercial vaccine) | 3 | 1.7 | 2.0 | 2.8 | 9.4 |
| Negative | 1 | 1.1 | 1.3 | 1.0 | 1.3 |
| control group | 2 | 1.0 | 0.9 | 0.9 | 0.9 |
| (1 ml PBS) | 3 | 0.7 | 1.1 | 1.2 | 0.7 |

[a]Pigs were divided into 5 groups for experiment, 3 pigs in each group. Different groups adopted different dose of Vaccine Composition A for vaccination. Each animal received two vaccination injections, with a 4 week interval between each time. Serum was taken 10 days after each injection. 1 ml PBS was injected for the blank control group.
[b]Simulation Index (SI): the counts per minute (cpm) of T-cell culture with simulation of FMDV protein/the counts per minute (cpm) of T-cell culture without simulation of FMDV protein. Simulation Index (SI) higher than 1.5 is defined as a positive response.

TABLE 5

T-cell Response in pigs received two vaccinations
of Vaccine Composition B to FMDV protein.

| Immunogen | Pig No. | First vaccination T-cell Stimulation Index (S.I.[b]) | | Second vaccination T-cell Stimulation Index (S.I.[b]) | |
|---|---|---|---|---|---|
| | | 10 μg/ml | 50 μg/ml | 10 μg/ml | 50 μg/ml |
| Vaccine | 1 | 1.2 | 2.0 | 3.0 | 8.9 |
| Composition B | 2 | 1.6 | 2.1 | 2.8 | 7.4 |
| 0.2 mg | 3 | 1.3 | 1.8 | 2.7 | 6.9 |
| Vaccine | 1 | 1.6 | 2.4 | 3.1 | 8.2 |
| Composition B | 2 | 1.4 | 2.2 | 3.6 | 8.7 |
| 0.5 mg | 3 | 1.3 | 2.2 | 3.1 | 7.7 |
| Vaccine | 1 | 1.7 | 2.3 | 3.3 | 8.1 |
| Composition B | 2 | 1.5 | 1.9 | 3.5 | 8.7 |
| 1 mg | 3 | 1.6 | 2.1 | 3.1 | 8.9 |
| Positive | 1 | 1.7 | 2.5 | 4.5 | 8.9 |
| control group | 2 | 1.4. | 2.7 | 3.1 | 9.5 |
| (Commercial vaccine) | 3 | 1.9 | 2.4 | 3.0 | 9.7 |
| Negative | 1 | 1.2 | 1.2 | 1.1 | 1.2 |
| control group | 2 | 0.9 | 0.8 | 1.2 | 1.4 |
| (1 ml PBS) | 3 | 0.8 | 1.0 | 0.8 | 0.9 |

[a]Pigs were divided into 5 groups for experiment, 3 pigs in each group. Different groups adopted different dose of Vaccine Composition B for vaccination. Each animal received two vaccination injections, with a 4 week interval between each time. Serum was taken 10 days after each injection. 1 ml PBS was injected for the blank control group.
[b]Simulation Index (SI): the counts per minute (cpm) of T-cell culture with simulation of FMDV protein/the counts per minute (cpm) of T-cell culture without simulation of FMDV protein. Simulation Index (SI) higher than 1.5 is defined as a positive response.

Table 4 and 5 illustrate the in vitro proliferative response of T-cells collected from pigs that were respectively vaccinated with Vaccine Composition A or Vaccine Composition B (200 μg, 500 μg and 1 mg of protein), the commercial anti-FMD vaccine or the buffer. The proliferative response was determined after in vitro simulation of 10 μg ml$^{-1}$ or 50 μg ml$^{-1}$ of FMDV protein. When simulated by 50 μg ml$^{-1}$ of viral protein, the T-cells from the pigs that were vaccinated with the recombinant protein and the commercial anti-FMD vaccine showed the best response, while the group simulated by buffer showed no proliferative response.

The results of the challenge of FMDV to pigs are shown in Tables 6 and 7.

TABLE 6

FMDV challenge analysis: 25 pigs (5 groups) were respectively vaccinated twice with 0.2 or 0.5 or 1 mg of protein (Vaccine Composition A), the commercial anti-FMD vaccine, or the buffer, and were then challenged by FMDV at a dose of 1000 times of the 50% Lethal Dose (LD$_{50}$).

| Samples tested | | Number of animals protected/ Number of animals challenged |
|---|---|---|
| Vaccine Composition A | 0.2 mg Protein | 4/5 |
| | 0.5 mg Protein | 5/5 |
| | 1 mg Protein | 5/5 |
| Commercial anti-FMD vaccine | | 5/5 |
| Buffer control group | | 0/5 |

TABLE 7

FMDV challenge analysis: 25 pigs (5 groups) were respectively vaccinated twice with 0.2 or 0.5 or 1 mg of protein (Vaccine Composition B), the commercial anti-FMD vaccine, or the buffer, and were then challenged by FMDV at a dose of 1000 times of the 50% Lethal Dose (LD$_{50}$).

| Samples tested | | Number of animals protected/ Number of animals challenged |
|---|---|---|
| Vaccine Composition B | 0.2 mg Protein | 5/5 |
| | 0.5 mg Protein | 5/5 |
| | 1 mg Protein | 5/5 |
| Commercial anti-FMD vaccine | | 5/5 |
| Buffer control group | | 0/5 |

Among the 5 groups of pigs challenged by FMDV, a rapid onset of disease was seen in the buffer control group (n=5). All of them were diagnosed as FMD positive based the occurrence of typical FMD symptoms within defined time limit (7-10 days). While the animals (n=5) in the positive control group of the commercial anti-FMD vaccine did not exhibit any FMD symptoms. As for the pigs (n=5) that were vaccinated with 0.2 mg of Vaccine Composition A, 4 of them were protected against FDMV challenge; all the pigs (n=5) that were vaccinated with 0.5 mg or 1 mg of Vaccine Composition A were completely protected against the FMDV challenge. The pigs (n=5) that were vaccinated with 0.2 mg, 0.5 mg or 1 mg of Vaccine Composition B were also completely protected against the FMDV challenge, and did not show any FMD symptoms.

I claim:

1. A vaccine composition comprising a recombinant protein comprising from its N-terminus to C-terminus:
    a tandem repeat of an antigenic epitope of the FMDV capsid protein;
    the constant region of the immunoglobulin heavy chain or a functional fragment thereof; and
    the FMDV 3D protein or an immunogenic fragment thereof.

2. The vaccine composition of claim 1, wherein said antigenic epitope in the recombinant protein is repeated for 2, 3, 4, or 5 times in the tandem repeat.

3. The vaccine composition of claim 1, wherein the antigenic epitopes are linked to each other via a peptide linker and/or wherein the tandem repeat of the antigenic epitope is linked to the constant region of the immunoglobulin heavy chain via a peptide linker.

4. The vaccine composition of claim 1, wherein said FMDV 3D protein comprises the amino acid sequence set forth in SEQ ID NO: 6.

5. The vaccine composition of claim 1, wherein said FMDV capsid protein is VP1.

6. The vaccine composition of claim 5, wherein said antigenic epitope of VP1 comprises one or more amino acid sequences selected from the group consisting of SEQ ID NO:9, SEQ ID NO:10, SEQ ID NO:25, SEQ ID NO:26, SEQ ID NO:32, SEQ ID NO:33, SEQ ID NO:34, SEQ ID NO:43, and SEQ ID NO:44.

7. The vaccine composition of claim 5, wherein said tandem repeat is a tandem repeat of two antigenic epitopes of VP1, wherein the amino acid sequences of the first and the second antigenic epitope of VP1 are respectively SEQ ID NO:9 and SEQ ID NO:10, SEQ ID NO:25 and SEQ ID NO:26, or SEQ ID NO:43 and SEQ ID NO:44; or said tandem repeat is a tandem repeat of three antigenic epitopes of VP1, wherein the amino acid sequences of the first, the second, and the third antigenic epitope of VP1 are respectively SEQ ID NO:32, SEQ ID NO:33, and SEQ ID NO:34.

8. The vaccine composition of claim 1, wherein said recombinant protein comprises an amino acid sequence selected from the group consisting of SEQ ID NO:8, SEQ ID NO:30, SEQ ID NO:41, and SEQ ID NO:47.

9. The vaccine composition of claim 1, wherein said immunoglobulin heavy chain is of pig, cattle, or sheep origin.

10. The vaccine composition of claim 1, further comprising a pharmaceutically acceptable carrier and/or adjuvant.

11. A vaccine composition comprising:
(i) a recombinant protein comprising from its N-terminus to C-terminus:
a tandem repeat of an antigenic epitope of the FMDV capsid protein; and
the constant region of the immunoglobulin heavy chain; and
(ii) the FMDV 3D protein or an immunogenic fragment thereof.

12. The vaccine composition of claim 11, wherein said antigenic epitope in the recombinant protein is repeated for 2, 3, 4, or 5 times in the tandem repeat.

13. The vaccine composition of claim 11, wherein the antigenic epitopes are linked to each other via a peptide linker and/or wherein the tandem repeat of the antigenic epitope is linked to the constant region of the immunoglobulin heavy chain via a peptide linker.

14. The vaccine composition of claim 11, wherein said FMDV 3D protein comprises the amino acid sequence set forth in SEQ ID NO: 6.

15. The vaccine composition of claim 11, wherein said FMDV capsid protein is VP1.

16. The vaccine composition of claim 15, wherein said antigenic epitope of VP1 comprises one or more amino acid sequences selected from the group consisting of SEQ ID NO:9, SEQ ID NO:10, SEQ ID NO:25, SEQ ID NO:26, SEQ ID NO:32, SEQ ID NO:33, SEQ ID NO:34, SEQ ID NO:43, and SEQ ID NO:44.

17. The vaccine composition of claim 15, wherein said tandem repeat is a tandem repeat of two antigenic epitopes of VP1, wherein the amino acid sequences of the first and the second antigenic epitope of VP1 are respectively SEQ ID NO:9 and SEQ ID NO:10, SEQ ID NO:25 and SEQ ID NO:26, or SEQ ID NO:43 and SEQ ID NO:44; or said tandem repeat is a tandem repeat of three antigenic epitopes of VP1, wherein the amino acid sequences of the first, the second, and the third antigenic epitope of VP1 are respectively SEQ ID NO:32, SEQ ID NO:33, and SEQ ID NO:34.

18. The vaccine composition of claim 11, wherein said recombinant protein comprises an amino acid sequence selected from the group consisting of SEQ ID NO:13, SEQ ID NO:28, SEQ ID NO:39, and SEQ ID NO:45.

19. The vaccine composition of claim 11, wherein said immunoglobulin heavy chain is of pig, cattle, or sheep origin.

20. The vaccine composition of claim 11, further comprising a pharmaceutically acceptable carrier and/or adjuvant.

21. An isolated polynucleotide encoding a recombinant protein comprising from its N-terminus to C-terminus:
a tandem repeat of an antigenic epitope of the FMDV capsid protein;
the constant region of the immunoglobulin heavy chain or a functional fragment thereof; and
the FMDV 3D protein or an immunogenic fragment.

22. The isolated polynucleotide of claim 21 comprising a nucleotide sequence selected from the group consisting of SEQ ID NO:7, SEQ ID NO:31, SEQ ID NO:42, and SEQ ID NO:48.

23. An isolated recombinant protein comprising the amino acid sequence encoded by the polynucleotide of claim 21.

24. A method of vaccinating an animal against FMDV comprising administering the vaccine composition of claim 8, wherein said constant region of said immunoglobulin heavy chain is from the same species as said animal.

25. A method of vaccinating an animal against FMDV comprising administering the vaccine composition of claim 18, wherein said constant region of said immunoglobulin heavy chain is from the same species as said animal.

26. An isolated recombinant protein comprising the amino acid sequence encoded by the polynucleotide of claim 22.

27. A method of vaccinating an animal against FMDV comprising administering the vaccine composition of claim 1, wherein said constant region of said immunoglobulin heavy chain is from the same species as said animal.

28. A method of vaccinating an animal against FMDV comprising administering the vaccine composition of claim 11, wherein said constant region of said immunoglobulin heavy chain is from the same species as said animal.

* * * * *

SEQUENCE LISTING

<160> NUMBER OF SEQ ID NOS: 48

<210> SEQ ID NO 1
<211> LENGTH: 417
<212> TYPE: DNA
<213> ORGANISM: artificial
<220> FEATURE:

```
<223> OTHER INFORMATION: DNA sequence encoding tandem repeats of FMDV
      VP1 epitopes with linkers

<400> SEQUENCE: 1
atggtaccaa acctgcgtgg tgacctgcag gtacttgctc agaaagttgc tcgtactctg      60
ccaggcggct ctagtggcgg acgccataaa caaaagattg tcgcgccggc aaaacaactc     120
ctgggtggta gttctggagg cgtaccaaac ctgcgtggtg acctgcaggt acttgctcag     180
aaagttgctc gtactctgcc aggtggttcg agcggtggcc ggcataaaca gaaaattgtc     240
gcacctgcaa acagctgtt gggaggttcg agcggtggcg taccaaacct gcgtggtgac      300
ctgcaggtac ttgctcagaa agttgctcgt actctgccag gtggttcgtc cggcggtcgg     360
cataaacaga aaattgtagc accggctaaa caactgctgg gcggttcggg aggctct        417

<210> SEQ ID NO 2
<211> LENGTH: 139
<212> TYPE: PRT
<213> ORGANISM: artificial
<220> FEATURE:
<223> OTHER INFORMATION: amino acid sequence of tandem repeats of FMDV
      VP1 epitopes with linkers

<400> SEQUENCE: 2

Met Val Pro Asn Leu Arg Gly Asp Leu Gln Val Leu Ala Gln Lys Val
1               5                   10                  15

Ala Arg Thr Leu Pro Gly Gly Ser Ser Gly Gly Arg His Lys Gln Lys
            20                  25                  30

Ile Val Ala Pro Ala Lys Gln Leu Leu Gly Gly Ser Ser Gly Gly Val
        35                  40                  45

Pro Asn Leu Arg Gly Asp Leu Gln Val Leu Ala Gln Lys Val Ala Arg
    50                  55                  60

Thr Leu Pro Gly Gly Ser Ser Gly Gly Arg His Lys Gln Lys Ile Val
65                  70                  75                  80

Ala Pro Ala Lys Gln Leu Leu Gly Gly Ser Ser Gly Gly Val Pro Asn
                85                  90                  95

Leu Arg Gly Asp Leu Gln Val Leu Ala Gln Lys Val Ala Arg Thr Leu
            100                 105                 110

Pro Gly Gly Ser Ser Gly Gly Arg His Lys Gln Lys Ile Val Ala Pro
        115                 120                 125

Ala Lys Gln Leu Leu Gly Gly Ser Ser Gly Gly
    130                 135

<210> SEQ ID NO 3
<211> LENGTH: 984
<212> TYPE: DNA
<213> ORGANISM: swine

<400> SEQUENCE: 3
gcccccaaga cggccccatc ggtctaccct ctggcccct gcggcaggga cgtgtctggc       60
cctaacgtgg ccttgggctg cctggcctca agctacttcc ccgagccagt gaccgtgacc     120
tggaactcgg gcgccctgac cagtggcgtg cacaccttcc catccgtcct gcagccgtca     180
gggctctact ccctcagcag catggtgacc gtgccggcca gcagcctgtc cagcaagagc     240
tacacctgca atgtcaacca cccggccacc accaccaagg tggacaagcg tgttggaata     300
caccagccgc aaacatgtcc catatgccca ggctgtgaag tggccggggc ctcggtcttc     360
atcttccctc caaacccaa ggacaccctc atgatctccc agacccccga ggtcacgtgc     420
gtggtggtgg acgtcagcaa ggagcacgcc gaggtccagt tctcctggta cgtggacggc     480
```

```
gtagaggtgc acacggccga gacgagacca aaggaggagc agttcaacag cacctaccgt    540
gtggtcagcg tcctgcccat ccagcaccag gactggctga aggggaagga gttcaagtgc    600
aaggtcaaca acgtagacct cccagccccc atcacgagga ccatctccaa ggctataggg    660
cagagccggg agccgcaggt gtacaccctg cccccacccg ccgaggagct gtccaggagc    720
aaagtcacgc taacctgcct ggtcattggc ttctacccac ctgacatcca tgttgagtgg    780
aagagcaacg gacagccgga gccagagaac acataccgca ccaccccgcc ccagcaggac    840
gtggacggga ccttcttcct gtacagcaaa ctcgcggtgg acaaggcaag atgggaccat    900
ggagacaaat ttgagtgtgc ggtgatgcac gaggctctgc acaaccacta cacccagaag    960
tccatctcca agactcaggg taaa                                           984
```

<210> SEQ ID NO 4
<211> LENGTH: 328
<212> TYPE: PRT
<213> ORGANISM: swine

<400> SEQUENCE: 4

```
Ala Pro Lys Thr Ala Pro Ser Val Tyr Pro Leu Ala Pro Cys Gly Arg
1               5                   10                  15

Asp Val Ser Gly Pro Asn Val Ala Leu Gly Cys Leu Ala Ser Ser Tyr
                20                  25                  30

Phe Pro Glu Pro Val Thr Val Thr Trp Asn Ser Gly Ala Leu Thr Ser
            35                  40                  45

Gly Val His Thr Phe Pro Ser Val Leu Gln Pro Ser Gly Leu Tyr Ser
        50                  55                  60

Leu Ser Ser Met Val Thr Val Pro Ala Ser Ser Leu Ser Ser Lys Ser
65                  70                  75                  80

Tyr Thr Cys Asn Val Asn His Pro Ala Thr Thr Thr Lys Val Asp Lys
                85                  90                  95

Arg Val Gly Ile His Gln Pro Gln Thr Cys Pro Ile Cys Pro Gly Cys
            100                 105                 110

Glu Val Ala Gly Pro Ser Val Phe Ile Phe Pro Pro Lys Pro Lys Asp
        115                 120                 125

Thr Leu Met Ile Ser Gln Thr Pro Glu Val Thr Cys Val Val Val Asp
    130                 135                 140

Val Ser Lys Glu His Ala Glu Val Gln Phe Ser Trp Tyr Val Asp Gly
145                 150                 155                 160

Val Glu Val His Thr Ala Glu Thr Arg Pro Lys Glu Glu Gln Phe Asn
                165                 170                 175

Ser Thr Tyr Arg Val Val Ser Val Leu Pro Ile Gln His Gln Asp Trp
            180                 185                 190

Leu Lys Gly Lys Glu Phe Lys Cys Lys Val Asn Asn Val Asp Leu Pro
        195                 200                 205

Ala Pro Ile Thr Arg Thr Ile Ser Lys Ala Ile Gly Gln Ser Arg Glu
    210                 215                 220

Pro Gln Val Tyr Thr Leu Pro Pro Ala Glu Glu Leu Ser Arg Ser
225                 230                 235                 240

Lys Val Thr Leu Thr Cys Leu Val Ile Gly Phe Tyr Pro Pro Asp Ile
                245                 250                 255

His Val Glu Trp Lys Ser Asn Gly Gln Pro Glu Pro Glu Asn Thr Tyr
            260                 265                 270

Arg Thr Thr Pro Pro Gln Gln Asp Val Asp Gly Thr Phe Phe Leu Tyr
        275                 280                 285
```

Ser Lys Leu Ala Val Asp Lys Ala Arg Trp Asp His Gly Asp Lys Phe
        290                 295                 300

Glu Cys Ala Val Met His Glu Ala Leu His Asn His Tyr Thr Gln Lys
305                 310                 315                 320

Ser Ile Ser Lys Thr Gln Gly Lys
            325

<210> SEQ ID NO 5
<211> LENGTH: 1413
<212> TYPE: DNA
<213> ORGANISM: Foot-and-mouth disease virus

<400> SEQUENCE: 5
gggttgatcg tcgacaccag agatgtggag gagcgtgtcc acgtgatgcg caaaaccaag      60
ctcgcgccca ccgtggcgca cggtgtgttc aaccctgagt tcgggcctgc cgctctgtcc     120
aacaaggacc gcgcctgaa cgaaggggtt gtccttgacg atgtcatttt ctccaaacac      180
aaaggagata caaggatgtc tgaagaggac aaagcgctgt tcggcgctg tgctgctgac      240 tacgcgtcgc gtctacacag tgtgttgggg acagcaaacg ccccactgag tgtgtatgaa     300
gccatcaaag gcgtcgacgg acttgacgcc atggagccgg acacggcgcc cggtctcccc     360
tgggctctcc aagggaaacg ccgcggcgcc ctgatcgact tcgaaaacgg caccgtcggg     420
cctgaggttg aggcagcact caagctcatg gaaagccgcg agtacaaatt cgtctgccaa     480
accttcctga aggacgaaat tcggccgcta gaaaaggtac gcgctggcaa gacacgcatt     540
gtcgacgtgt tgcctgttga acacattctc tacaccagaa tgatgattgg cagattctgt     600
gctcagatgc attcaaacaa cggaccgcaa attggatcag cggtcggttg taaccctgac     660
gttgattggc aaagatttgg cacacatttc gcccagtaca aaaacgtgtg ggatgtggac     720
tactcagcct ttgatgcaaa ccactgcagc gatgcgatga catcatgtt cgaggaagtg     780 ttccgcacgg agttcggatt ccaccccgaac gccgagtgga ttctgaagac tctagtgaac     840
acggagcacg cttacgagaa caagcgcatt gttgttgaag gtggaatgcc gtccggttgt     900
tccgcaacaa gcatcatcaa cacaattttg aacaacatct acgtgcttta cgccctgcgt     960
aggcactatg agggagtcga gctggacact acaccatga tctcttatgg agacgacatc     1020
gtggtggcaa gtgactacga cctggacttt gaggctctca gccccacctt caagtccctt     1080
ggtcagacta tcactccggc cgacaaaagc gacaaggtt tgttcttgg tcactccata     1140 accgacgtca ctttcctcaa aagacacttc acatgggact acggaactgg gttttacaaa     1200
cctgtgatgg cctcgaagac cctcgaggcc atcctctcct ttgcacgccg tgggaccata     1260
caggagaagt tgatctccgt ggcaggactc gccgtccact ccggacctga tgaataccgg     1320
cgcctctttg agcccttcca aggcctcttc gagattccaa gctacagatc actttacctg     1380
cgatgggtga acgccgtgtg cggtgacgca taa                                  1413

<210> SEQ ID NO 6
<211> LENGTH: 470
<212> TYPE: PRT
<213> ORGANISM: Foot-and-mouth disease virus

<400> SEQUENCE: 6

Gly Leu Ile Val Asp Thr Arg Asp Val Glu Glu Arg Val His Val Met
1               5                   10                  15

Arg Lys Thr Lys Leu Ala Pro Thr Val Ala His Gly Val Phe Asn Pro
            20                  25                  30

```
Glu Phe Gly Pro Ala Ala Leu Ser Asn Lys Asp Pro Arg Leu Asn Glu
         35                  40                  45

Gly Val Val Leu Asp Asp Val Ile Phe Ser Lys His Lys Gly Asp Thr
 50                  55                  60

Arg Met Ser Glu Glu Asp Lys Ala Leu Phe Arg Arg Cys Ala Ala Asp
 65                  70                  75                  80

Tyr Ala Ser Arg Leu His Ser Val Leu Gly Thr Ala Asn Ala Pro Leu
                 85                  90                  95

Ser Val Tyr Glu Ala Ile Lys Gly Val Asp Gly Leu Asp Ala Met Glu
                100                 105                 110

Pro Asp Thr Ala Pro Gly Leu Pro Trp Ala Leu Gln Gly Lys Arg Arg
             115                 120                 125

Gly Ala Leu Ile Asp Phe Glu Asn Gly Thr Val Gly Pro Glu Val Glu
 130                 135                 140

Ala Ala Leu Lys Leu Met Glu Ser Arg Glu Tyr Lys Phe Val Cys Gln
145                 150                 155                 160

Thr Phe Leu Lys Asp Glu Ile Arg Pro Leu Glu Lys Val Arg Ala Gly
                165                 170                 175

Lys Thr Arg Ile Val Asp Val Leu Pro Val Glu His Ile Leu Tyr Thr
             180                 185                 190

Arg Met Met Ile Gly Arg Phe Cys Ala Gln Met His Ser Asn Asn Gly
             195                 200                 205

Pro Gln Ile Gly Ser Ala Val Gly Cys Asn Pro Asp Val Asp Trp Gln
210                 215                 220

Arg Phe Gly Thr His Phe Ala Gln Tyr Lys Asn Val Trp Asp Val Asp
225                 230                 235                 240

Tyr Ser Ala Phe Asp Ala Asn His Cys Ser Asp Ala Met Asn Ile Met
                245                 250                 255

Phe Glu Glu Val Phe Arg Thr Glu Phe Gly Phe His Pro Asn Ala Glu
             260                 265                 270

Trp Ile Leu Lys Thr Leu Val Asn Thr Glu His Ala Tyr Glu Asn Lys
             275                 280                 285

Arg Ile Val Val Glu Gly Gly Met Pro Ser Gly Cys Ser Ala Thr Ser
290                 295                 300

Ile Ile Asn Thr Ile Leu Asn Asn Ile Tyr Val Leu Tyr Ala Leu Arg
305                 310                 315                 320

Arg His Tyr Glu Gly Val Glu Leu Asp Thr Tyr Thr Met Ile Ser Tyr
                325                 330                 335

Gly Asp Asp Ile Val Val Ala Ser Asp Tyr Asp Leu Asp Phe Glu Ala
             340                 345                 350

Leu Lys Pro His Phe Lys Ser Leu Gly Gln Thr Ile Thr Pro Ala Asp
             355                 360                 365

Lys Ser Asp Lys Gly Phe Val Leu Gly His Ser Ile Thr Asp Val Thr
370                 375                 380

Phe Leu Lys Arg His Phe His Met Asp Tyr Gly Thr Gly Phe Tyr Lys
385                 390                 395                 400

Pro Val Met Ala Ser Lys Thr Leu Glu Ala Ile Leu Ser Phe Ala Arg
                405                 410                 415

Arg Gly Thr Ile Gln Glu Lys Leu Ile Ser Val Ala Gly Leu Ala Val
             420                 425                 430

His Ser Gly Pro Asp Glu Tyr Arg Arg Leu Phe Glu Pro Phe Gln Gly
             435                 440                 445

Leu Phe Glu Ile Pro Ser Tyr Arg Ser Leu Tyr Leu Arg Trp Val Asn
450                 455                 460
```

Ala Val Cys Gly Asp Ala
465             470

<210> SEQ ID NO 7
<211> LENGTH: 2814
<212> TYPE: DNA
<213> ORGANISM: artificial
<220> FEATURE:
<223> OTHER INFORMATION: DNA sequence encoding the recombinant protein

<400> SEQUENCE: 7

| | | | | | |
|---|---|---|---|---|---|
| atggtaccaa | acctgcgtgg | tgacctgcag | gtacttgctc | agaaagttgc | tcgtactctg | 60 |
| ccaggcggct | ctagtggcgg | acgccataaa | caaaagattg | tcgcgccggc | aaaacaactc | 120 |
| ctgggtggta | gttctggagg | cgtaccaaac | ctgcgtggtg | acctgcaggt | acttgctcag | 180 |
| aaagttgctc | gtactctgcc | aggtggttcg | agcggtggcc | ggcataaaca | gaaaattgtc | 240 |
| gcacctgcaa | acagctgtt | gggaggttcg | agcggtggcg | taccaaacct | gcgtggtgac | 300 |
| ctgcaggtac | ttgctcagaa | agttgctcgt | actctgccag | gtggttcgtc | cggcggtcgg | 360 |
| cataaacaga | aaattgtagc | accggctaaa | caactgctgg | gcggttcggg | aggtctgcc | 420 |
| cccaagacgg | ccccatcggt | ctaccctctg | gcccctgcg | gcaggacgt | gtctggccct | 480 |
| aacgtggcct | tgggctgcct | ggcctcaagc | tacttcccg | agccagtgac | cgtgacctgg | 540 |
| aactcgggcg | ccctgaccag | tggcgtgcac | accttccat | ccgtcctgca | gccgtcaggg | 600 |
| ctctactccc | tcagcagcat | ggtgaccgtg | ccggccagca | gcctgtccag | caagagctac | 660 |
| acctgcaatg | tcaaccaccc | ggccaccacc | accaaggtgg | acaagcgtgt | tggaatacac | 720 |
| cagccgcaaa | catgtcccat | atgcccaggc | tgtgaagtgg | ccgggccctc | ggtcttcatc | 780 |
| ttccctccaa | acccaagga | caccctcatg | atctcccaga | cccccgaggt | cacgtgcgtg | 840 |
| gtggtggacg | tcagcaagga | gcacgccgag | gtccagttct | cctggtacgt | ggacggcgta | 900 |
| gaggtgcaca | cggccgagac | agaccaaag | gaggagcagt | tcaacagcac | ctaccgtgtg | 960 |
| gtcagcgtcc | tgcccatcca | gcaccaggac | tggctgaagg | gaaggagtt | caagtgcaag | 1020 |
| gtcaacaacg | tagacctccc | agcccccatc | acgaggacca | tctccaaggc | tatagggcag | 1080 |
| agccgggagc | cgcaggtgta | caccctgccc | ccacccgccg | aggagctgtc | caggagcaaa | 1140 |
| gtcacgctaa | cctgcctggt | cattggcttc | tacccacctg | acatccatgt | tgagtggaag | 1200 |
| agcaacggac | agccggagcc | agagaacaca | taccgcacca | ccccgcccca | gcaggacgtg | 1260 |
| gacgggacct | tcttcctgta | cagcaaactc | gcggtggaca | aggcaagatg | ggaccatgga | 1320 |
| gacaaatttg | agtgtgcggt | gatgcacgag | gctctgcaca | accactacac | ccagaagtcc | 1380 |
| atctccaaga | ctcagggtaa | agggttgatc | gtcgacacca | gagatgtgga | ggagcgtgtc | 1440 |
| cacgtgatgc | gcaaaaccaa | gctcgcgccc | accgtggcgc | acggtgtgtt | caaccctgag | 1500 |
| ttcgggcctg | ccgctctgtc | caacaaggac | ccgcgcctga | cgaaggggt | gtccttgac | 1560 |
| gatgtcattt | tctccaaaca | caaggagat | acaaggatgt | ctgaagagga | caaagcgctg | 1620 |
| tttcggcgct | gtgctgctga | ctacgcgtcg | cgtctacaca | gtgtgttggg | gacagcaaac | 1680 |
| gccccactga | gtgtgtatga | agccatcaaa | ggcgtcgacg | gacttgacgc | catggagccg | 1740 |
| gacacgcgcg | ccggtctccc | ctgggctctc | aagggaaac | gccgcggcgc | cctgatcgac | 1800 |
| ttcgaaaacg | gcaccgtcgg | gcctgaggtt | gaggcagcac | tcaagctcat | ggaaagccgc | 1860 |
| gagtacaaat | tgtctgcca | aaccttcctg | aaggacgaaa | ttcggccgct | agaaaaggta | 1920 |
| cgcgctggca | agacacgcat | tgtcgacgtg | ttgcctgttg | aacacattct | ctacaccaga | 1980 |

```
atgatgattg gcagattctg tgctcagatg cattcaaaca acggaccgca aattggatca    2040
gcggtcggtt gtaaccctga cgttgattgg caaagatttg gcacacattt cgcccagtac    2100
aaaaacgtgt gggatgtgga ctactcagcc tttgatgcaa accactgcag cgatgcgatg    2160
aacatcatgt tcgaggaagt gttccgcacg gagttcggat tccacccgaa cgccgagtgg    2220
attctgaaga ctctagtgaa cacggagcac gcttacgaga caagcgcat tgttgttgaa     2280 ggtggaatgc cgtccggttg ttccgcaaca agcatcatca acacaattt  gaacaacatc    2340 tacgtgcttt acgccctgcg taggcactat gagggagtcg agctggacac ttacaccatg    2400
atctcttatg gagacgacat cgtggtggca agtgactacg acctggactt tgaggctctc    2460 aagcccccact tcaagtccct tggtcagact atcactccgg ccgacaaaag cgacaaggt    2520 tttgttcttg gtcactccat aaccgacgtc actttcctca aaagacactt ccacatggac    2580
tacggaactg ggttttacaa acctgtgatg gcctcgaaga ccctcgaggc catcctctcc    2640
tttgcacgcc gtgggaccat acaggagaag ttgatctccg tggcaggact cgccgtccac    2700
tccggacctg atgaataccg cgcctctttt gagcccttcc aaggcctctt cgagattcca    2760
agctacagat cactttacct gcgatgggtg aacgccgtgt gcggtgacgc ataa          2814
```

```
<210> SEQ ID NO 8
<211> LENGTH: 899
<212> TYPE: PRT
<213> ORGANISM: artificial
<220> FEATURE:
<223> OTHER INFORMATION: amino acid sequence of the recombinant protein

<400> SEQUENCE: 8

Met Val Pro Asn Leu Arg Gly Asp Leu Gln Val Leu Ala Gln Lys Val
1               5                   10                  15

Ala Arg Thr Leu Pro Gly Gly Ser Ser Gly Gly Arg His Lys Gln Lys
            20                  25                  30

Ile Val Ala Pro Ala Lys Gln Leu Leu Gly Gly Ser Ser Gly Gly Val
        35                  40                  45

Pro Asn Leu Arg Gly Asp Leu Gln Val Leu Ala Gln Lys Val Ala Arg
    50                  55                  60

Thr Leu Pro Gly Gly Ser Ser Gly Gly Arg His Lys Gln Lys Ile Val
65                  70                  75                  80

Ala Pro Ala Lys Gln Leu Leu Gly Gly Ser Ser Gly Gly Val Pro Asn
                85                  90                  95

Leu Arg Gly Asp Leu Gln Val Leu Ala Gln Lys Val Ala Arg Thr Leu
            100                 105                 110

Pro Gly Gly Ser Ser Gly Gly Arg His Lys Gln Lys Ile Val Ala Pro
        115                 120                 125

Ala Lys Gln Leu Leu Gly Gly Ser Ser Gly Gly Ala Pro Lys Thr Ala
    130                 135                 140

Pro Ser Val Tyr Pro Leu Ala Pro Cys Gly Arg Asp Val Ser Gly Pro
145                 150                 155                 160

Asn Val Ala Leu Gly Cys Leu Ala Ser Ser Tyr Phe Pro Glu Pro Val
                165                 170                 175

Thr Val Thr Trp Asn Ser Gly Ala Leu Thr Ser Gly Val His Thr Phe
            180                 185                 190

Pro Ser Val Leu Gln Pro Ser Gly Leu Tyr Ser Leu Ser Ser Met Val
        195                 200                 205

Thr Val Pro Ala Ser Ser Leu Ser Ser Lys Ser Tyr Thr Cys Asn Val
    210                 215                 220
```

-continued

```
Asn His Pro Ala Thr Thr Thr Lys Val Asp Lys Arg Val Gly Ile His
225                 230                 235                 240

Gln Pro Gln Thr Cys Pro Ile Cys Pro Gly Cys Glu Val Ala Gly Pro
            245                 250                 255

Ser Val Phe Ile Phe Pro Pro Lys Pro Lys Asp Thr Leu Met Ile Ser
        260                 265                 270

Gln Thr Pro Glu Val Thr Cys Val Val Asp Val Ser Lys Glu His
    275                 280                 285

Ala Glu Val Gln Phe Ser Trp Tyr Val Asp Gly Val Glu Val His Thr
290                 295                 300

Ala Glu Thr Arg Pro Lys Glu Glu Gln Phe Asn Ser Thr Tyr Arg Val
305                 310                 315                 320

Val Ser Val Leu Pro Ile Gln His Gln Asp Trp Leu Lys Gly Lys Glu
            325                 330                 335

Phe Lys Cys Lys Val Asn Asn Val Asp Leu Pro Ala Pro Ile Thr Arg
        340                 345                 350

Thr Ile Ser Lys Ala Ile Gly Gln Ser Arg Glu Pro Gln Val Tyr Thr
    355                 360                 365

Leu Pro Pro Pro Ala Glu Glu Leu Ser Arg Ser Lys Val Thr Leu Thr
370                 375                 380

Cys Leu Val Ile Gly Phe Tyr Pro Pro Asp Ile His Val Glu Trp Lys
385                 390                 395                 400

Ser Asn Gly Gln Pro Glu Pro Glu Asn Thr Tyr Arg Thr Thr Pro Pro
            405                 410                 415

Gln Gln Asp Val Asp Gly Thr Phe Phe Leu Tyr Ser Lys Leu Ala Val
        420                 425                 430

Asp Lys Ala Arg Trp Asp His Gly Asp Lys Phe Glu Cys Ala Val Met
    435                 440                 445

His Glu Ala Leu His Asn His Tyr Thr Gln Lys Ser Ile Ser Lys Thr
    450                 455                 460

Gln Gly Lys Gly Leu Ile Val Asp Thr Arg Asp Val Glu Glu Arg Val
465                 470                 475                 480

His Val Met Arg Lys Thr Lys Leu Ala Pro Thr Val Ala His Gly Val
            485                 490                 495

Phe Asn Pro Glu Phe Gly Pro Ala Ala Leu Ser Asn Lys Asp Pro Arg
        500                 505                 510

Leu Asn Glu Gly Val Val Leu Asp Asp Val Ile Phe Ser Lys His Lys
    515                 520                 525

Gly Asp Thr Arg Met Ser Glu Glu Asp Lys Ala Leu Phe Arg Arg Cys
530                 535                 540

Ala Ala Asp Tyr Ala Ser Arg Leu His Ser Val Leu Gly Thr Ala Asn
545                 550                 555                 560

Ala Pro Leu Ser Val Tyr Glu Ala Ile Lys Gly Val Asp Gly Leu Asp
            565                 570                 575

Ala Met Glu Pro Asp Thr Ala Pro Gly Leu Pro Trp Ala Leu Gln Gly
        580                 585                 590

Lys Arg Arg Gly Ala Leu Ile Asp Phe Glu Asn Gly Thr Val Gly Pro
    595                 600                 605

Glu Val Glu Ala Ala Leu Lys Leu Met Glu Ser Arg Glu Tyr Lys Phe
610                 615                 620

Val Cys Gln Thr Phe Leu Lys Asp Glu Ile Arg Pro Leu Glu Lys Val
625                 630                 635                 640

Arg Ala Gly Lys Thr Arg Ile Val Asp Val Leu Pro Val Glu His Ile
            645                 650                 655
```

```
Leu Tyr Thr Arg Met Met Ile Gly Arg Phe Cys Ala Gln Met His Ser
            660                 665                 670

Asn Asn Gly Pro Gln Ile Gly Ser Ala Val Gly Cys Asn Pro Asp Val
        675                 680                 685

Asp Trp Gln Arg Phe Gly Thr His Phe Ala Gln Tyr Lys Asn Val Trp
    690                 695                 700

Asp Val Asp Tyr Ser Ala Phe Asp Ala Asn His Cys Ser Asp Ala Met
705                 710                 715                 720

Asn Ile Met Phe Glu Glu Val Phe Arg Thr Glu Phe Gly Phe His Pro
                725                 730                 735

Asn Ala Glu Trp Ile Leu Lys Thr Leu Val Asn Thr Glu His Ala Tyr
            740                 745                 750

Glu Asn Lys Arg Ile Val Val Glu Gly Gly Met Pro Ser Gly Cys Ser
        755                 760                 765

Ala Thr Ser Ile Ile Asn Thr Ile Leu Asn Asn Ile Tyr Val Leu Tyr
    770                 775                 780

Ala Leu Arg Arg His Tyr Glu Gly Val Glu Leu Asp Thr Tyr Thr Met
785                 790                 795                 800

Ile Ser Tyr Gly Asp Asp Ile Val Val Ala Ser Asp Tyr Asp Leu Asp
                805                 810                 815

Phe Glu Ala Leu Lys Pro His Phe Lys Ser Leu Gly Gln Thr Ile Thr
            820                 825                 830

Pro Ala Asp Lys Ser Asp Lys Gly Phe Val Leu Gly His Ser Ile Thr
        835                 840                 845

Asp Val Thr Phe Leu Lys Arg His Phe His Met Asp Tyr Gly Thr Gly
    850                 855                 860

Phe Tyr Lys Pro Val Met Ala Ser Lys Thr Leu Glu Ala Ile Leu Ser
865                 870                 875                 880

Phe Ala Arg Arg Gly Thr Ile Gln Glu Lys Leu Ile Ser Val Ala Gly
                885                 890                 895

Leu Ala Val

<210> SEQ ID NO 9
<211> LENGTH: 20
<212> TYPE: PRT
<213> ORGANISM: Foot-and-mouth disease virus

<400> SEQUENCE: 9

Val Pro Asn Leu Arg Gly Asp Leu Gln Val Leu Ala Gln Lys Val Ala
1               5                   10                  15

Arg Thr Leu Pro
            20

<210> SEQ ID NO 10
<211> LENGTH: 14
<212> TYPE: PRT
<213> ORGANISM: Foot-and-mouth disease virus

<400> SEQUENCE: 10

Arg His Lys Gln Lys Ile Val Ala Pro Ala Lys Gln Leu Leu
1               5                   10

<210> SEQ ID NO 11
<211> LENGTH: 6
<212> TYPE: PRT
<213> ORGANISM: artificial
<220> FEATURE:
<223> OTHER INFORMATION: linker
```

<400> SEQUENCE: 11

Gly Gly Ser Ser Gly Gly
1               5

<210> SEQ ID NO 12
<211> LENGTH: 9
<212> TYPE: PRT
<213> ORGANISM: artificial
<220> FEATURE:
<223> OTHER INFORMATION: linker

<400> SEQUENCE: 12

Gly Gly Gly Ser Gly Gly Gly Gly Ser
1               5

<210> SEQ ID NO 13
<211> LENGTH: 467
<212> TYPE: PRT
<213> ORGANISM: artificial
<220> FEATURE:
<223> OTHER INFORMATION: amino acid sequence of the recombinant protein

<400> SEQUENCE: 13

Met Val Pro Asn Leu Arg Gly Asp Leu Gln Val Leu Ala Gln Lys Val
1               5                   10                  15

Ala Arg Thr Leu Pro Gly Gly Ser Ser Gly Gly Arg His Lys Gln Lys
            20                  25                  30

Ile Val Ala Pro Ala Lys Gln Leu Leu Gly Gly Ser Ser Gly Gly Val
        35                  40                  45

Pro Asn Leu Arg Gly Asp Leu Gln Val Leu Ala Gln Lys Val Ala Arg
    50                  55                  60

Thr Leu Pro Gly Gly Ser Ser Gly Gly Arg His Lys Gln Lys Ile Val
65                  70                  75                  80

Ala Pro Ala Lys Gln Leu Leu Gly Gly Ser Ser Gly Gly Val Pro Asn
                85                  90                  95

Leu Arg Gly Asp Leu Gln Val Leu Ala Gln Lys Val Ala Arg Thr Leu
            100                 105                 110

Pro Gly Gly Ser Ser Gly Gly Arg His Lys Gln Lys Ile Val Ala Pro
        115                 120                 125

Ala Lys Gln Leu Leu Gly Gly Ser Ser Gly Gly Ala Pro Lys Thr Ala
    130                 135                 140

Pro Ser Val Tyr Pro Leu Ala Pro Cys Gly Arg Asp Val Ser Gly Pro
145                 150                 155                 160

Asn Val Ala Leu Gly Cys Leu Ala Ser Ser Tyr Phe Pro Glu Pro Val
                165                 170                 175

Thr Val Thr Trp Asn Ser Gly Ala Leu Thr Ser Gly Val His Thr Phe
            180                 185                 190

Pro Ser Val Leu Gln Pro Ser Gly Leu Tyr Ser Leu Ser Ser Met Val
        195                 200                 205

Thr Val Pro Ala Ser Ser Leu Ser Ser Lys Ser Tyr Thr Cys Asn Val
    210                 215                 220

Asn His Pro Ala Thr Thr Thr Lys Val Asp Lys Arg Val Gly Ile His
225                 230                 235                 240

Gln Pro Gln Thr Cys Pro Ile Cys Pro Gly Cys Glu Val Ala Gly Pro
                245                 250                 255

Ser Val Phe Ile Phe Pro Pro Lys Pro Lys Asp Thr Leu Met Ile Ser
            260                 265                 270

```
Gln Thr Pro Glu Val Thr Cys Val Val Val Asp Val Ser Lys Glu His
        275                 280                 285
Ala Glu Val Gln Phe Ser Trp Tyr Val Asp Gly Val Glu Val His Thr
    290                 295                 300
Ala Glu Thr Arg Pro Lys Glu Glu Gln Phe Asn Ser Thr Tyr Arg Val
305                 310                 315                 320
Val Ser Val Leu Pro Ile Gln His Gln Asp Trp Leu Lys Gly Lys Glu
                325                 330                 335
Phe Lys Cys Lys Val Asn Asn Val Asp Leu Pro Ala Pro Ile Thr Arg
            340                 345                 350
Thr Ile Ser Lys Ala Ile Gly Gln Ser Arg Pro Gln Val Tyr Thr
        355                 360                 365
Leu Pro Pro Pro Ala Glu Glu Leu Ser Arg Ser Lys Val Thr Leu Thr
    370                 375                 380
Cys Leu Val Ile Gly Phe Tyr Pro Pro Asp Ile His Val Glu Trp Lys
385                 390                 395                 400
Ser Asn Gly Gln Pro Glu Pro Glu Asn Thr Tyr Arg Thr Thr Pro Pro
                405                 410                 415
Gln Gln Asp Val Asp Gly Thr Phe Phe Leu Tyr Ser Lys Leu Ala Val
            420                 425                 430
Asp Lys Ala Arg Trp Asp His Gly Asp Lys Phe Glu Cys Ala Val Met
        435                 440                 445
His Glu Ala Leu His Asn His Tyr Thr Gln Lys Ser Ile Ser Lys Thr
    450                 455                 460
Gln Gly Lys
465

<210> SEQ ID NO 14
<211> LENGTH: 1401
<212> TYPE: DNA
<213> ORGANISM: artificial
<220> FEATURE:
<223> OTHER INFORMATION: DNA sequence encoding the recombinant protein

<400> SEQUENCE: 14
atggtaccaa acctgcgtgg tgacctgcag gtacttgctc agaaagttgc tcgtactctg      60
ccaggcggct ctagtggcgg acgccataaa caaaagattg tcgcgccggc aaaacaactc     120
ctgggtggta gttctggagg cgtaccaaac ctgcgtggtg acctgcaggt acttgctcag     180
aaagttgctc gtactctgcc aggtggttcg agcggtggcc ggcataaaca gaaaattgtc     240
gcacctgcaa acagctgtt gggaggttcg agcggtggcg taccaaacct gcgtggtgac     300
ctgcaggtac ttgctcagaa agttgctcgt actctgccag gtggttcgtc cggcggtcgg     360
cataaacaga aaattgtagc accggctaaa caactgctgg gcggttcggg aggctctgcc     420
cccaagacgg ccccatcggt ctaccctctg gcccctgcg gcagggacgt gtctggccct     480
aacgtggcct tgggctgcct ggcctcaagc tacttccccg agccagtgac cgtgacctgg     540
aactcgggcg ccctgaccag tggcgtgcac accttcccat ccgtcctgca gccgtcaggg     600
ctctactccc tcagcagcat ggtgaccgtg ccggccagca gcctgtccag caagagctac     660
acctgcaatg tcaaccaccc ggccaccacc accaaggtgg acaagcgtgt tgaatacac     720 cagccgcaaa catgtcccat atgcccaggc tgtgaagtgg ccgggccctc ggtcttcatc     780
ttccctccaa acccaaggg cacccctcat gatctcccaga ccccccgaggt cacgtgcgtg     840 gtggtggacg tcagcaagga gcacgccgag gtccagttct cctggtacgt ggacggcgta     900
gaggtgcaca cggccgagac gagaccaaag gaggagcagt tcaacagcac ctaccgtgtg     960
```

-continued

```
gtcagcgtcc tgcccatcca gcaccaggac tggctgaagg ggaaggagtt caagtgcaag    1020
gtcaacaacg tagacctccc agcccccatc acgaggacca tctccaaggc tatagggcag    1080
agccgggagc cgcaggtgta caccctgccc ccacccgccg aggagctgtc caggagcaaa    1140
gtcacgctaa cctgcctggt cattggcttc tacccacctg acatccatgt tgagtggaag    1200
agcaacggac agccggagcc agagaacaca taccgcacca ccccgcccca gcaggacgtg    1260
gacgggacct tcttcctgta cagcaaactc gcggtggaca aggcaagatg ggaccatgga    1320
gacaaatttg agtgtgcggt gatgcacgag gctctgcaca accactacac ccagaagtcc    1380
atctccaaga ctcagggtaa a                                              1401
```

<210> SEQ ID NO 15
<211> LENGTH: 18
<212> TYPE: DNA
<213> ORGANISM: artificial
<220> FEATURE:
<223> OTHER INFORMATION: scIgG 5'primer

<400> SEQUENCE: 15

```
gcccccaaga cggcccca                                                  18
```

<210> SEQ ID NO 16
<211> LENGTH: 18
<212> TYPE: DNA
<213> ORGANISM: artificial
<220> FEATURE:
<223> OTHER INFORMATION: scIgG 3' primer

<400> SEQUENCE: 16

```
tcatcattta ccctgagt                                                  18
```

<210> SEQ ID NO 17
<211> LENGTH: 41
<212> TYPE: DNA
<213> ORGANISM: artificial
<220> FEATURE:
<223> OTHER INFORMATION: 3D 5' primer

<400> SEQUENCE: 17

```
ccatctccaa gactcagggt aaagggttga tcgtcgacac c                        41
```

<210> SEQ ID NO 18
<211> LENGTH: 16
<212> TYPE: DNA
<213> ORGANISM: artificial
<220> FEATURE:
<223> OTHER INFORMATION: 3D 3' primer

<400> SEQUENCE: 18

```
gtatgcgtca ccgcac                                                    16
```

<210> SEQ ID NO 19
<211> LENGTH: 25
<212> TYPE: DNA
<213> ORGANISM: artificial
<220> FEATURE:
<223> OTHER INFORMATION: 3R-IGCD 5' primer

<400> SEQUENCE: 19

```
agctgaattc atggtaccaa acctg                                          25
```

<210> SEQ ID NO 20
<211> LENGTH: 41

```
<212> TYPE: DNA
<213> ORGANISM: artificial
<220> FEATURE:
<223> OTHER INFORMATION: 3R-IGC 3' primer1

<400> SEQUENCE: 20
ggtagaggtt ctgagtccca tttcccaact agcagctgtg g                          41

<210> SEQ ID NO 21
<211> LENGTH: 41
<212> TYPE: DNA
<213> ORGANISM: artificial
<220> FEATURE:
<223> OTHER INFORMATION: D 5' primer

<400> SEQUENCE: 21
ccatctccaa gactcagggt aaagggttga tcgtcgacac c                          41

<210> SEQ ID NO 22
<211> LENGTH: 29
<212> TYPE: DNA
<213> ORGANISM: artificial
<220> FEATURE:
<223> OTHER INFORMATION: 3R-IGCD 3' primer

<400> SEQUENCE: 22
agcttctaga aatttatgcg tcaccgcac                                        29

<210> SEQ ID NO 23
<211> LENGTH: 22
<212> TYPE: DNA
<213> ORGANISM: artificial
<220> FEATURE:
<223> OTHER INFORMATION: 3R-IGC 5'primer

<400> SEQUENCE: 23
agctgaattc atggtaccaa ac                                               22

<210> SEQ ID NO 24
<211> LENGTH: 28
<212> TYPE: DNA
<213> ORGANISM: artificial
<220> FEATURE:
<223> OTHER INFORMATION: 3R-IGC 3'primer2

<400> SEQUENCE: 24
agcttctaga tcatcattta ccctgagt                                         28

<210> SEQ ID NO 25
<211> LENGTH: 26
<212> TYPE: PRT
<213> ORGANISM: Foot-and-mouth disease virus

<400> SEQUENCE: 25

Lys Thr Thr Tyr Gly Glu Thr Thr Ala Arg Arg Asp Asp Thr Ala Ala
1               5                   10                  15

Leu Ala Gln Arg Leu Ser Gly Arg Leu Pro
            20                  25

<210> SEQ ID NO 26
<211> LENGTH: 14
<212> TYPE: PRT
<213> ORGANISM: Foot-and-mouth disease virus

<400> SEQUENCE: 26

Arg Arg Lys Gln Glu Ile Ile Ala Pro Glu Lys Gln Met Val
```

```
1               5                  10
```

<210> SEQ ID NO 27
<211> LENGTH: 5
<212> TYPE: PRT
<213> ORGANISM: artificial
<220> FEATURE:
<223> OTHER INFORMATION: linker

<400> SEQUENCE: 27

```
Gly Gly Gly Gly Ser
1               5
```

<210> SEQ ID NO 28
<211> LENGTH: 486
<212> TYPE: PRT
<213> ORGANISM: artificial
<220> FEATURE:
<223> OTHER INFORMATION: amino acid sequence of the recombinant protein

<400> SEQUENCE: 28

```
Met Lys Thr Thr Tyr Gly Glu Thr Thr Ala Arg Arg Asp Asp Thr Ala
1               5                   10                  15

Ala Leu Ala Gln Arg Leu Ser Gly Arg Leu Pro Gly Gly Ser Ser Gly
            20                  25                  30

Gly Arg Arg Lys Gln Glu Ile Ile Ala Pro Glu Lys Gln Met Val Gly
        35                  40                  45

Gly Ser Ser Gly Gly Lys Thr Thr Tyr Gly Glu Thr Thr Ala Arg Arg
    50                  55                  60

Asp Asp Thr Ala Ala Leu Ala Gln Arg Leu Ser Gly Arg Leu Pro Gly
65                  70                  75                  80

Gly Ser Ser Gly Gly Arg Arg Lys Gln Glu Ile Ile Ala Pro Glu Lys
                85                  90                  95

Gln Met Val Gly Gly Ser Ser Gly Gly Lys Thr Thr Tyr Gly Glu Thr
            100                 105                 110

Thr Ala Arg Arg Asp Asp Thr Ala Ala Leu Ala Gln Arg Leu Ser Gly
        115                 120                 125

Arg Leu Pro Gly Gly Ser Ser Gly Gly Arg Arg Lys Gln Glu Ile Ile
    130                 135                 140

Ala Pro Glu Lys Gln Met Val Gly Gly Gly Ser Lys Leu Ala Pro
145                 150                 155                 160

Lys Thr Ala Pro Ser Val Tyr Pro Leu Ala Pro Cys Gly Arg Asp Thr
                165                 170                 175

Ser Gly Pro Asn Val Ala Leu Gly Cys Leu Ala Ser Ser Tyr Phe Pro
            180                 185                 190

Glu Pro Val Thr Met Thr Trp Asn Ser Gly Ala Leu Thr Ser Gly Val
        195                 200                 205

His Thr Phe Pro Ser Val Leu Gln Pro Ser Gly Leu Tyr Ser Leu Ser
    210                 215                 220

Ser Met Val Thr Val Pro Ala Ser Ser Leu Ser Ser Lys Ser Tyr Thr
225                 230                 235                 240

Cys Asn Val Asn His Pro Ala Thr Thr Thr Lys Val Asp Lys Arg Val
                245                 250                 255

Gly Thr Lys Thr Lys Pro Pro Cys Pro Ile Cys Pro Gly Cys Glu Val
            260                 265                 270

Ala Gly Pro Ser Val Phe Ile Phe Pro Pro Lys Pro Lys Asp Thr Leu
        275                 280                 285

Met Ile Ser Gln Thr Pro Glu Val Thr Cys Val Val Val Asp Val Ser
```

| | | | | | | | | | | | | | |
|---|---|---|---|---|---|---|---|---|---|---|---|---|---|
| | | 290 | | | | 295 | | | | 300 | | | |
| Lys | Glu | His | Ala | Glu | Val | Gln | Phe | Ser | Trp | Tyr | Val | Asp | Gly | Val | Glu |
| 305 | | | | 310 | | | | 315 | | | | 320 |

Lys Glu His Ala Glu Val Gln Phe Ser Trp Tyr Val Asp Gly Val Glu
305                 310                 315                 320

Val His Thr Ala Glu Thr Arg Pro Lys Glu Glu Gln Phe Asn Ser Thr
            325                 330                 335

Tyr Arg Val Val Ser Val Leu Pro Ile Gln His Gln Asp Trp Leu Lys
            340                 345                 350

Gly Lys Glu Phe Lys Cys Lys Val Asn Asn Val Asp Leu Pro Ala Pro
            355                 360                 365

Ile Thr Arg Thr Ile Ser Lys Ala Ile Gly Gln Ser Arg Glu Pro Gln
        370                 375                 380

Val Tyr Thr Leu Pro Pro Pro Ala Glu Glu Leu Ser Arg Ser Lys Val
385                 390                 395                 400

Thr Val Thr Cys Leu Val Ile Gly Phe Tyr Pro Pro Asp Ile His Val
                405                 410                 415

Glu Trp Lys Ser Asn Gly Gln Pro Glu Pro Gly Asn Tyr Arg Thr
            420                 425                 430

Thr Pro Pro Gln Gln Asp Val Asp Gly Thr Phe Phe Leu Tyr Ser Lys
            435                 440                 445

Leu Ala Val Asp Lys Ala Arg Trp Asp His Gly Glu Thr Phe Glu Cys
450                 455                 460

Ala Val Met His Glu Ala Leu His Asn His Tyr Thr Gln Lys Ser Ile
465                 470                 475                 480

Ser Lys Thr Gln Gly Lys
            485

<210> SEQ ID NO 29
<211> LENGTH: 1461
<212> TYPE: DNA
<213> ORGANISM: artificial
<220> FEATURE:
<223> OTHER INFORMATION: DNA sequence encoding the recombinant protein

<400> SEQUENCE: 29

```
atgaagacca cctatggcga aacgactgca cgtcgtgatg acacagctgc gcttgcacag      60
cgcctgagcg gtagactgcc cggtggaagt tcgggtggtc gtcgcaaaca ggaaatcatt     120
gcgccggaga agcaaatggt gggcggcagt tcgggcggca aaactacgta cggggaaacc     180
acggcccgtc gtgatgatac agcagctctg cccaacgtc tctcaggtcg cctgccaggt      240
gggagttcag gaggcaggcg taagcaggag attattgcgc agaaaagca atggtgggt      300
gggagctccg gtgggaaaac cacgtatggg gaaaccactg cgagacgcga tgatacagcc    360
gcactggctc agaggttgtc tggccgctta cctggtgggt ctagcggagg tcgtcggaaa    420
caggaaatca tagccccgga gaacagatg gtcggtgggg gtggcagcaa gcttgccccc     480
aagacggccc catcggtcta ccctctggcc cctgcggca gggacacgtc tggccctaac     540
gtggccttgg gctgcctggc ctcaagctac ttccccgagc cagtgaccat gacctggaac    600
tcgggcgccc tgaccagtgg cgtgcatacc ttcccatccg tcctgcagcc gtcagggctc    660
tactccctca gcagcatggt gaccgtgccg gccagcagcc tgtccagcaa gagctacacc    720
tgcaatgtca accaccggc caccaccacc aaggtggaca gcgtgttgg aacaaagacc      780
aaaccaccat gtcccatatg cccaggctgt gaagtggccg ggccctcggt cttcatcttc    840
cctccaaaac ccaaggacac cctcatgatc tcccagaccc ccgaggtcac gtgcgtggtg    900
gtggacgtca gcaaggagca cgccgaggtc cagttctcct ggtacgtgga cggcgtagag    960
```

-continued

```
gtgcacacgg ccgagacgag accaaaggag gagcagttca acagcaccta ccgtgtggtc      1020
agcgtcctgc ccatccagca ccaggactgg ctgaagggga aggagttcaa gtgcaaggtc      1080
aacaacgtag acctcccagc ccccatcacg aggaccatct ccaaggctat agggcagagc      1140
cgggagccgc agtgtacac cctgccccca cccgccgagg agctgtccag gagcaaagtc       1200
accgtaacct gcctggtcat tggcttctac ccacctgaca tccatgttga gtggaagagc      1260 aacgacagc cggagccaga gggcaattac cgcaccaccc cgccccagca ggacgtggac       1320
gggaccttct tcctgtacag caagctcgcg gtggacaagg caagatggga ccatggagaa      1380
acatttgagt gtgcggtgat gcacgaggct ctgcacaacc actacaccca gaagtccatc      1440
tccaagactc agggtaaatg a                                                1461
```

<210> SEQ ID NO 30
<211> LENGTH: 956
<212> TYPE: PRT
<213> ORGANISM: artificial
<220> FEATURE:
<223> OTHER INFORMATION: amino acid sequence of the recombinant protein

<400> SEQUENCE: 30

```
Met Lys Thr Thr Tyr Gly Glu Thr Thr Ala Arg Arg Asp Asp Thr Ala
1               5                  10                  15

Ala Leu Ala Gln Arg Leu Ser Gly Arg Leu Pro Gly Gly Ser Ser Gly
            20                  25                  30

Gly Arg Arg Lys Gln Glu Ile Ile Ala Pro Glu Lys Gln Met Val Gly
        35                  40                  45

Gly Ser Ser Gly Gly Lys Thr Thr Tyr Gly Glu Thr Thr Ala Arg Arg
    50                  55                  60

Asp Asp Thr Ala Ala Leu Ala Gln Arg Leu Ser Gly Arg Leu Pro Gly
65                  70                  75                  80

Gly Ser Ser Gly Gly Arg Arg Lys Gln Glu Ile Ile Ala Pro Glu Lys
                85                  90                  95

Gln Met Val Gly Gly Ser Ser Gly Gly Lys Thr Thr Tyr Gly Glu Thr
            100                 105                 110

Thr Ala Arg Arg Asp Asp Thr Ala Ala Leu Ala Gln Arg Leu Ser Gly
        115                 120                 125

Arg Leu Pro Gly Gly Ser Ser Gly Gly Arg Arg Lys Gln Glu Ile Ile
    130                 135                 140

Ala Pro Glu Lys Gln Met Val Gly Gly Gly Ser Lys Leu Ala Pro
145                 150                 155                 160

Lys Thr Ala Pro Ser Val Tyr Pro Leu Ala Pro Cys Gly Arg Asp Thr
                165                 170                 175

Ser Gly Pro Asn Val Ala Leu Gly Cys Leu Ala Ser Ser Tyr Phe Pro
            180                 185                 190

Glu Pro Val Thr Met Thr Trp Asn Ser Gly Ala Leu Thr Ser Gly Val
        195                 200                 205

His Thr Phe Pro Ser Val Leu Gln Pro Ser Gly Leu Tyr Ser Leu Ser
    210                 215                 220

Ser Met Val Thr Val Pro Ala Ser Ser Leu Ser Ser Lys Ser Tyr Thr
225                 230                 235                 240

Cys Asn Val Asn His Pro Ala Thr Thr Lys Val Asp Lys Arg Val
                245                 250                 255

Gly Thr Lys Thr Lys Pro Pro Cys Pro Thr Cys Pro Gly Cys Glu Val
            260                 265                 270

Ala Gly Pro Ser Val Phe Ile Phe Pro Pro Lys Pro Lys Asp Thr Leu
```

```
                275                 280                 285
Met Ile Ser Gln Thr Pro Glu Val Thr Cys Val Val Asp Val Ser
290                 295                 300

Lys Glu His Ala Glu Val Gln Phe Ser Trp Tyr Val Asp Gly Val Glu
305                 310                 315                 320

Val His Thr Ala Glu Thr Arg Pro Lys Glu Glu Gln Phe Asn Ser Thr
                325                 330                 335

Tyr Arg Val Val Ser Val Leu Pro Ile Gln His Gln Asp Trp Leu Lys
                340                 345                 350

Gly Lys Glu Phe Lys Cys Lys Val Asn Asn Val Asp Leu Pro Ala Pro
                355                 360                 365

Ile Thr Arg Thr Ile Ser Lys Ala Ile Gly Gln Ser Arg Glu Pro Gln
370                 375                 380

Val Tyr Thr Leu Pro Pro Ala Glu Glu Leu Ser Arg Ser Lys Val
385                 390                 395                 400

Thr Val Thr Cys Leu Val Ile Gly Phe Tyr Pro Pro Asp Ile His Val
                405                 410                 415

Glu Trp Lys Ser Asn Gly Gln Pro Glu Pro Glu Gly Asn Tyr Arg Thr
                420                 425                 430

Thr Pro Pro Gln Gln Asp Val Asp Gly Thr Phe Phe Leu Tyr Ser Lys
                435                 440                 445

Leu Ala Val Asp Lys Ala Arg Trp Asp His Gly Glu Thr Phe Glu Cys
450                 455                 460

Ala Val Met His Glu Ala Leu His Asn His Tyr Thr Gln Lys Ser Ile
465                 470                 475                 480

Ser Lys Thr Gln Gly Lys Gly Leu Ile Val Asp Thr Arg Asp Val Glu
                485                 490                 495

Glu Arg Val His Val Met Arg Lys Thr Lys Leu Ala Pro Thr Val Ala
                500                 505                 510

His Gly Val Phe Asn Pro Glu Phe Gly Pro Ala Ala Leu Ser Asn Lys
                515                 520                 525

Asp Pro Arg Leu Asn Glu Gly Val Val Leu Asp Asp Val Ile Phe Ser
530                 535                 540

Lys His Lys Gly Asp Thr Arg Met Ser Glu Glu Asp Lys Ala Leu Phe
545                 550                 555                 560

Arg Arg Cys Ala Ala Asp Tyr Ala Ser Arg Leu His Ser Val Leu Gly
                565                 570                 575

Thr Ala Asn Ala Pro Leu Ser Val Tyr Glu Ala Ile Lys Gly Val Asp
                580                 585                 590

Gly Leu Asp Ala Met Glu Pro Asp Thr Ala Pro Gly Leu Pro Trp Ala
                595                 600                 605

Leu Gln Gly Lys Arg Arg Gly Ala Leu Ile Asp Phe Glu Asn Gly Thr
610                 615                 620

Val Gly Pro Glu Val Glu Ala Ala Leu Lys Leu Met Glu Ser Arg Glu
625                 630                 635                 640

Tyr Lys Phe Val Cys Gln Thr Phe Leu Lys Asp Glu Ile Arg Pro Leu
                645                 650                 655

Glu Lys Val Arg Ala Gly Lys Thr Arg Ile Val Asp Val Leu Pro Val
                660                 665                 670

Glu His Ile Leu Tyr Thr Arg Met Met Ile Gly Arg Phe Cys Ala Gln
                675                 680                 685

Met His Ser Asn Asn Gly Pro Gln Ile Gly Ser Ala Val Gly Cys Asn
690                 695                 700
```

```
Pro Asp Val Asp Trp Gln Arg Phe Gly Thr His Phe Ala Gln Tyr Lys
705                 710                 715                 720

Asn Val Trp Asp Val Asp Tyr Ser Ala Phe Asp Ala Asn His Cys Ser
            725                 730                 735

Asp Ala Met Asn Ile Met Phe Glu Glu Val Phe Arg Thr Glu Phe Gly
        740                 745                 750

Phe His Pro Asn Ala Glu Trp Ile Leu Lys Thr Leu Val Asn Thr Glu
    755                 760                 765

His Ala Tyr Glu Asn Lys Arg Ile Val Val Glu Gly Met Pro Ser
770                 775                 780

Gly Cys Ser Ala Thr Ser Ile Ile Asn Thr Ile Leu Asn Asn Ile Tyr
785                 790                 795                 800

Val Leu Tyr Ala Leu Arg Arg His Tyr Glu Gly Val Glu Leu Asp Thr
                805                 810                 815

Tyr Thr Met Ile Ser Tyr Gly Asp Ile Val Val Ala Ser Asp Tyr
            820                 825                 830

Asp Leu Asp Phe Glu Ala Leu Lys Pro His Phe Lys Ser Leu Gly Gln
        835                 840                 845

Thr Ile Thr Pro Ala Asp Lys Ser Asp Lys Gly Phe Val Leu Gly His
    850                 855                 860

Ser Ile Thr Asp Val Thr Phe Leu Lys Arg His Phe His Met Asp Tyr
865                 870                 875                 880

Gly Thr Gly Phe Tyr Lys Pro Val Met Ala Ser Lys Thr Leu Glu Ala
                885                 890                 895

Ile Leu Ser Phe Ala Arg Arg Gly Thr Ile Gln Glu Lys Leu Ile Ser
            900                 905                 910

Val Ala Gly Leu Ala Val His Ser Gly Pro Asp Glu Tyr Arg Arg Leu
        915                 920                 925

Phe Glu Pro Phe Gln Gly Leu Phe Glu Ile Pro Ser Tyr Arg Ser Leu
    930                 935                 940

Tyr Leu Arg Trp Val Asn Ala Val Cys Gly Asp Ala
945                 950                 955

<210> SEQ ID NO 31
<211> LENGTH: 2868
<212> TYPE: DNA
<213> ORGANISM: artificial
<220> FEATURE:
<223> OTHER INFORMATION: DNA sequence encoding the recombinant protein

<400> SEQUENCE: 31
atgaagacca cctatggcga aacgactgca cgtcgtgatg acacagctgc gcttgcacag      60
cgcctgagcg gtagactgcc cggtggaagt tcgggtggtc gtcgcaaaca ggaaatcatt     120
gcgccggaga agcaaatggt gggcggcagt tcgggcggca aaactacgta cggggaaacc     180
acggcccgtc gtgatgatac agcagctctg gcccaacgtc tctcaggtcg cctgccaggt     240
gggagttcag gaggcaggcg taagcaggag attattgcgc agaaaagca atggtgggt      300 gggagctccg gtgggaaaac cacgtatggg gaaaccactg cgagacgcga tgatacagcc     360
gcactggctc agaggttgtc tggccgctta cctggtgggt ctagcggagg tcgtcggaaa     420
caggaaatca tagccccgga gaaacagatg gtcggtgggg gtggcagcaa gcttgccccc     480
aagacggccc catcggtcta ccctctggcc cctgcggca gggacacgtc tggccctaac      540
gtggccttgg gctgcctggc ctcaagctac ttccccgagc cagtgaccat gacctggaac     600
tcgggcgccc tgaccagtgg cgtgcatacc ttcccatccg tcctgcagcc gtcagggctc     660
```

```
tactccctca gcagcatggt gaccgtgccg gccagcagcc tgtccagcaa gagctacacc    720
tgcaatgtca accacccggc caccaccacc aaggtggaca gcgtgttgg  aacaaagacc    780
aaaccaccat gtcccacatg cccaggctgt gaagtggccg ggccctcggt cttcatcttc    840
cctccaaaac ccaaggacac cctcatgatc tcccagaccc ccgaggtcac gtgcgtggtg    900
gtggacgtca gcaaggagca cgccgaggtc cagttctcct ggtacgtgga cggcgtagag    960
gtgcacacgg ccgagacgag accaaaggag gagcagttca acagcaccta ccgtgtggtc   1020
agcgtcctgc ccatccagca ccaggactgg ctgaagggga aggagttcaa gtgcaaggtc   1080
aacaacgtag acctcccagc ccccatcacg gaggaccatct ccaaggctat agggcagagc   1140
cgggagccgc aggtgtacac cctgccccca cccgccgagg agctgtccag gagcaaagtc   1200
accgtaacct gcctggtcat tggcttctac ccacctgaca tccatgttga gtggaagagc   1260
aacggacagc cggagccaga gggcaattac cgcaccaccc cgccccagca ggacgtggac   1320
gggaccttct tcctgtacag caagctcgcg gtggacaagg caagatggga ccatggagaa   1380
acatttgagt gtgcggtgat gcacgaggct ctgcacaacc actacaccca gaagtccatc   1440
tccaagactc agggtaaagg gttgatcgtc gacaccagag atgtggagga gcgtgtccac   1500
gtgatgcgca aaaccaagct cgcgcccacc gtggcgcacg gtgtgttcaa ccctgagttc   1560
gggcctgccg ctctgtccaa caaggacccg cgcctgaacg aaggggttgt ccttgacgat   1620
gtcattttct ccaaacacaa aggagataca aggatgtctg aagaggacaa agcgctgttt   1680
cggcgctgtg ctgctgacta cgcgtcgcgt ctacacagtg tgttggggac agcaaacgcc   1740
ccactgagtg tgtatgaagc catcaaaggc gtcgacggac ttgacgccat ggagccggac   1800
acggcgcccg gtctccctg gctctccaa gggaaacgcc gcggcgccct gatcgacttc   1860
gaaaacggca ccgtcgggcc tgaggttgag gcagcactca agctcatgga aagccgcgag   1920
tacaaattcg tctgccaaac cttcctgaag gacgaaattc ggccgctaga aaaggtacgc   1980
gctggcaaga cacgcattgt cgacgtgttg cctgttgaac acattctcta caccagaatg   2040
atgattggca gattctgtgc tcagatgcat tcaaacaacg gaccgcaaat tggatcagcg   2100
gtcggttgta accctgacgt tgattggcaa agatttggca cacatttcgc ccagtacaaa   2160
aacgtgtggg atgtggacta ctcagccttt gatgcaaacc actgcagcga tgcgatgaac   2220
atcatgttcg aggaagtgtt ccgcacggag ttcggattcc acccgaacgc cgagtggatt   2280
ctgaagactc tagtgaacac ggagcacgct tacgagaaca gcgcattgt tgttgaaggt   2340
ggaatgccgt ccgttgttc  cgcaacaagc atcatcaaca caattttgaa caacatctac   2400
gtgctttacg ccctgcgtag gcactatgag ggagtcgagc tggacactta ccatgatc    2460
tcttatggag acgacatcgt ggtggcaagt gactacgacc tggactttga ggctctcaag   2520
ccccacttca gtcccttgg  tcagactatc actccggccg acaaaagcga caaaggtttt   2580
gttcttggtc actccataac cgacgtcact ttcctcaaaa gacacttcca catggactac   2640
ggaactgggt tttacaaacc tgtgatggcc tcgaagaccc ttgaggccat cctctccttt   2700
gcacgccgtg gaccataca ggagaagttg atctccgtgg caggactcgc cgtccactcc   2760
ggacctgatg aataccggcg cctctttgag ccctccaag gcctcttcga gattccaagc   2820
tacagatcac tttacctgcg atgggtgaac gccgtgtgcg gtgacgca                2868
```

<210> SEQ ID NO 32
<211> LENGTH: 20
<212> TYPE: PRT
<213> ORGANISM: Foot-and-mouth disease virus

```
<400> SEQUENCE: 32

Val Ser Asn Val Arg Gly Asp Leu Gln Val Leu Ala Gln Lys Ala Glu
1               5                   10                  15

Arg Ala Leu Pro
            20

<210> SEQ ID NO 33
<211> LENGTH: 20
<212> TYPE: PRT
<213> ORGANISM: Foot-and-mouth disease virus

<400> SEQUENCE: 33

Thr Asn Asn Val Arg Gly Asp Leu Gln Val Leu Ala Gln Lys Ala Glu
1               5                   10                  15

Arg Ala Leu Pro
            20

<210> SEQ ID NO 34
<211> LENGTH: 14
<212> TYPE: PRT
<213> ORGANISM: Foot-and-mouth disease virus

<400> SEQUENCE: 34

Arg His Lys Gln Lys Ile Val Ala Pro Ala Lys Gln Leu Leu
1               5                   10

<210> SEQ ID NO 35
<211> LENGTH: 32
<212> TYPE: DNA
<213> ORGANISM: artificial
<220> FEATURE:
<223> OTHER INFORMATION: cIGC 5'primer

<400> SEQUENCE: 35
catgaagctt gcctccacca cagccccgaa ag                                      32

<210> SEQ ID NO 36
<211> LENGTH: 38
<212> TYPE: DNA
<213> ORGANISM: artificial
<220> FEATURE:
<223> OTHER INFORMATION: cIGC 3' primer

<400> SEQUENCE: 36
ccggctcgag tttacccgca gacttagagg tggacttc                                38

<210> SEQ ID NO 37
<211> LENGTH: 330
<212> TYPE: PRT
<213> ORGANISM: cattle

<400> SEQUENCE: 37

Ala Ser Thr Thr Ala Pro Lys Val Tyr Pro Leu Ser Ser Cys Cys Gly
1               5                   10                  15

Asp Lys Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Ala Ser Ser Ser Gly Thr Gln Thr
65                  70                  75                  80
```

| | | | | | | | | | | | |
|---|---|---|---|---|---|---|---|---|---|---|---|
|Phe|Thr|Cys|Asn|Val|Ala|His|Pro|Ala|Ser|Ser|Thr|Lys|Val|Asp|Lys|
| | | | |85| | | | |90| | | | |95| |
|Ala|Val|Asp|Pro|Thr|Cys|Lys|Pro|Ser|Pro|Cys|Asp|Cys|Cys|Pro|Pro|
| | | |100| | | | |105| | | | |110| | |
|Pro|Glu|Leu|Pro|Gly|Gly|Pro|Ser|Val|Phe|Ile|Phe|Pro|Pro|Lys|Pro|
| | |115| | | | |120| | | | |125| | | |
|Lys|Asp|Thr|Leu|Thr|Ile|Ser|Gly|Thr|Pro|Glu|Val|Thr|Cys|Val|Val|
| |130| | | | |135| | | | |140| | | | |
|Val|Asp|Val|Gly|His|Asp|Asp|Pro|Glu|Val|Lys|Phe|Ser|Trp|Phe|Val|
|145| | | | |150| | | | |155| | | | |160|
|Asp|Asp|Val|Glu|Val|Asn|Thr|Ala|Thr|Thr|Lys|Pro|Arg|Glu|Glu|Gln|
| | | | |165| | | | |170| | | | |175| |
|Phe|Asn|Ser|Thr|Tyr|Arg|Val|Val|Ser|Ala|Leu|Arg|Ile|Gln|His|Gln|
| | | |180| | | | |185| | | | |190| | |
|Asp|Trp|Thr|Gly|Gly|Lys|Glu|Phe|Lys|Cys|Lys|Val|His|Asn|Glu|Gly|
| | |195| | | | |200| | | | |205| | | |
|Leu|Pro|Ala|Pro|Ile|Val|Arg|Thr|Ile|Ser|Arg|Thr|Lys|Gly|Pro|Ala|
| |210| | | | |215| | | | |220| | | | |
|Arg|Glu|Pro|Gln|Val|Tyr|Val|Leu|Ala|Pro|Pro|Gln|Glu|Glu|Leu|Ser|
|225| | | | |230| | | | |235| | | | |240|
|Lys|Ser|Thr|Val|Ser|Leu|Thr|Cys|Met|Val|Thr|Ser|Phe|Tyr|Pro|Asp|
| | | | |245| | | | |250| | | | |255| |
|Tyr|Ile|Ala|Val|Glu|Trp|Gln|Arg|Asn|Gly|Gln|Pro|Glu|Ser|Glu|Asp|
| | | |260| | | | |265| | | | |270| | |
|Lys|Tyr|Gly|Thr|Thr|Pro|Pro|Gln|Leu|Asp|Ala|Asp|Ser|Ser|Tyr|Phe|
| | |275| | | | |280| | | | |285| | | |
|Leu|Tyr|Ser|Lys|Leu|Arg|Val|Asp|Arg|Asn|Ser|Trp|Gln|Glu|Gly|Asp|
| |290| | | | |295| | | | |300| | | | |
|Thr|Tyr|Thr|Cys|Val|Val|Met|His|Glu|Ala|Leu|His|Asn|His|Tyr|Thr|
|305| | | | |310| | | | |315| | | | |320|
|Gln|Lys|Ser|Thr|Ser|Lys|Ser|Ala|Gly|Lys| | | | | | |
| | | |325| | | | |330| | | | | | | |

```
<210> SEQ ID NO 38
<211> LENGTH: 990
<212> TYPE: DNA
<213> ORGANISM: cattle

<400> SEQUENCE: 38
gcctccacca cagccccgaa agtctaccct ctgagttctt gctgcgggga caagtccagc      60
tccaccgtga ccctgggctg cctggtctcc agctacatgc ccgagccggt gaccgtgacc     120
tggaactcgg gtgccctgaa gagcggcgtg cacaccttcc cggctgtcct tcagtcctcc     180
gggctgtact ctctcagcag catggtgacc gtgcccgcca gcagctcagg aacccagacc     240
ttcacctgca acgtagccca cccggccagc agcaccaagg tggacaaggc tgttgatccc     300
acatgcaaac catcaccctg tgactgttgc ccaccccctg agctcccggg aggaccctct     360
gtcttcatct tccaccgaa acccaaggac accctcacaa tctcgggaac gcccgaggtc     420
acgtgtgtgg tggtggacgt gggccacgat gaccccgagg tgaagttctc ctggttcgtg     480
gacgacgtgg aggtaaacac agccacgacg aagccgagag aggagcagtt caacagcacc     540
taccgcgtgg tcagcgccct gcgcatccag caccaggact ggactggagg aaaggagttc     600
aagtgcaagg tccacaacga aggctcccg gccccatcg tgaggaccat ctccaggacc     660
aaagggccgg cccgggagcc gcaggtgtat gtcctggccc cacccagga agagctcagc     720
```

```
aaaagcacgg tcagcctcac ctgcatggtc accagcttct acccagacta catcgccgtg    780
gagtggcaga gaaacgggca gcctgagtcg gaggacaagt acggcacgac cccgccccag    840
ctggacgccg acagctccta cttcctgtac agcaagctca gggtggacag aacagctgg     900 caggaaggag acacctacac gtgtgtggtg atgcacgagg ccctgcacaa tcactacacg    960
cagaagtcca cctctaagtc tgcgggtaaa                                     990
```

<210> SEQ ID NO 39
<211> LENGTH: 470
<212> TYPE: PRT
<213> ORGANISM: artificial
<220> FEATURE:
<223> OTHER INFORMATION: amino acid sequence of the recombinant protein

<400> SEQUENCE: 39

```
Met Val Ser Asn Val Arg Gly Asp Leu Gln Val Leu Ala Gln Lys Ala
1               5                  10                  15

Glu Arg Ala Leu Pro Gly Gly Ser Ser Gly Gly Arg His Lys Gln Lys
            20                  25                  30

Ile Val Ala Pro Ala Lys Gln Leu Leu Gly Gly Ser Gly Gly Thr
        35                  40                  45

Asn Asn Val Arg Gly Asp Leu Gln Val Leu Ala Gln Lys Ala Glu Arg
50                  55                  60

Ala Leu Pro Gly Gly Ser Gly Gly Arg His Lys Gln Lys Ile Val
65                  70                  75                  80

Ala Pro Ala Lys Gln Leu Leu Gly Gly Ser Ser Gly Gly Thr Asn Asn
                85                  90                  95

Val Arg Gly Asp Leu Gln Val Leu Ala Gln Lys Ala Glu Arg Ala Leu
            100                 105                 110

Pro Gly Gly Ser Ser Gly Gly Arg His Lys Gln Lys Ile Val Ala Pro
        115                 120                 125

Ala Lys Gln Leu Leu Gly Gly Gly Ser Lys Leu Ala Ser Thr Thr
    130                 135                 140

Ala Pro Lys Val Tyr Pro Leu Ser Ser Cys Cys Gly Asp Lys Ser Ser
145                 150                 155                 160

Ser Thr Val Thr Leu Gly Cys Leu Val Ser Ser Tyr Met Pro Glu Pro
                165                 170                 175

Val Thr Val Thr Trp Asn Ser Gly Ala Leu Lys Ser Gly Val His Thr
            180                 185                 190

Phe Pro Ala Val Leu Gln Ser Ser Gly Leu Tyr Ser Leu Ser Ser Met
        195                 200                 205

Val Thr Val Pro Ala Ser Ser Ser Gly Thr Gln Thr Phe Thr Cys Asn
    210                 215                 220

Val Ala His Pro Ala Ser Ser Thr Lys Val Asp Lys Ala Val Asp Pro
225                 230                 235                 240

Thr Cys Lys Pro Ser Pro Cys Asp Cys Cys Pro Pro Glu Leu Pro
                245                 250                 255

Gly Gly Pro Ser Val Phe Ile Phe Pro Pro Lys Pro Lys Asp Thr Leu
            260                 265                 270

Thr Ile Ser Gly Thr Pro Glu Val Thr Cys Val Val Val Asp Val Gly
        275                 280                 285

His Asp Asp Pro Glu Val Lys Phe Ser Trp Phe Val Asp Asp Val Glu
    290                 295                 300

Val Asn Thr Ala Thr Thr Lys Pro Arg Glu Glu Gln Phe Asn Ser Thr
305                 310                 315                 320
```

```
Tyr Arg Val Val Ser Ala Leu Arg Ile Gln His Gln Asp Trp Thr Gly
            325                 330                 335
Gly Lys Glu Phe Lys Cys Lys Val His Asn Glu Gly Leu Pro Ala Pro
                340                 345                 350
Ile Val Arg Thr Ile Ser Arg Thr Lys Gly Pro Ala Arg Glu Pro Gln
            355                 360                 365
Val Tyr Val Leu Ala Pro Pro Gln Glu Glu Leu Ser Lys Ser Thr Val
        370                 375                 380
Ser Leu Thr Cys Met Val Thr Ser Phe Tyr Pro Asp Tyr Ile Ala Val
385                 390                 395                 400
Glu Trp Gln Arg Asn Gly Gln Pro Glu Ser Glu Asp Lys Tyr Gly Thr
                405                 410                 415
Thr Pro Pro Gln Leu Asp Ala Asp Ser Ser Tyr Phe Leu Tyr Ser Lys
            420                 425                 430
Leu Arg Val Asp Arg Asn Ser Trp Gln Glu Gly Asp Thr Tyr Thr Cys
        435                 440                 445
Val Val Met His Glu Ala Leu His Asn His Tyr Thr Gln Lys Ser Thr
450                 455                 460
Ser Lys Ser Ala Gly Lys
465                 470

<210> SEQ ID NO 40
<211> LENGTH: 1413
<212> TYPE: DNA
<213> ORGANISM: artificial
<220> FEATURE:
<223> OTHER INFORMATION: DNA sequence encoding the recombinant protein

<400> SEQUENCE: 40
atggtgagca acgtgcgcgg agatctccaa gtgctggctc aaaaagcaga acgtgcactg      60
ccgggcggct ctagtggcgg acgccataaa caaaagattg tcgcgccggc aaaacaactc     120
ctgggtggta gttctggagg caccaataac gtgcgcggcg atctgcaggt cctggcgcaa     180
aaagcggaac gtgctctgcc gggtggttcg agcggtggcc ggcataaaca gaaaattgtc     240
gcacctgcaa acagctgtt gggaggttcg agcggtggca ccaataatgt gcgcggcgac     300
ttgcaagtgc tggctcagaa ggcggaacgc gcattgcctg tggttcgtc cggcggtcgg     360 cataaacaga aaattgtagc accggctaaa caactgctgg gcggtggagg ctctaagctt     420
gcctccacca cagccccgaa agtctaccct ctgagttctt gctgcgggga caagtccagc     480
tccaccgtga ccctgggctg cctggtctcc agctacatgc cgagccggt gaccgtgacc     540 tggaactcgg gtgccctgaa gagcggcgtg cacaccttcc cggctgtcct tcagtcctcc     600
gggctgtact ctctcagcag catggtgacc gtgcccgcca gcagctcagg aacccagacc     660
ttcacctgca acgtagccca cccggccagc agcaccaagg tggacaaggc tgttgatccc     720
acatgcaaac catcaccctg tgactgttgc ccaccccctg agctccccgg aggaccctct     780
gtcttcatct tccccaccgaa acccaaggac accctcacaa tctcgggaac gcccgaggtc     840
acgtgtgtgg tggtggacgt gggccacgat gaccccgagg tgaagttctc ctggttcgtg     900
gacgacgtgg aggtaaacac agccacgacg aagccgagag aggagcagtt caacagcacc     960
taccgcgtgg tcagcgccct gcgcatccag caccaggact ggactggagg aaaggagttc    1020
aagtgcaagg tccacaacga aggcctcccg gcccccatcg tgaggaccat ctccaggacc    1080
aaagggccgg cccgggagcc gcaggtgtat gtcctggccc cacccccagga agagctcagc    1140 aaaagcacgg tcagcctcac ctgcatggtc accagcttct acccagacta catcgccgtg    1200
```

-continued

```
gagtggcaga gaaacgggca gcctgagtcg gaggacaagt acggcacgac cccgccccag  1260
ctggacgccg acagtcccta cttcctgtac agcaagctca gggtggacag gaacagctgg  1320
caggaaggag acacctacac gtgtgtggtg atgcacgagg ccctgcacaa tcactacacg  1380
cagaagtcca cctctaagtc tgcgggtaaa tga                               1413
```

<210> SEQ ID NO 41
<211> LENGTH: 940
<212> TYPE: PRT
<213> ORGANISM: artificial
<220> FEATURE:
<223> OTHER INFORMATION: amino acid sequence of the recombinant protein

<400> SEQUENCE: 41

```
Met Val Ser Asn Val Arg Gly Asp Leu Gln Val Leu Ala Gln Lys Ala
1               5                   10                  15

Glu Arg Ala Leu Pro Gly Gly Ser Gly Gly Arg His Lys Gln Lys
            20                  25                  30

Ile Val Ala Pro Ala Lys Gln Leu Leu Gly Gly Ser Ser Gly Gly Thr
        35                  40                  45

Asn Asn Val Arg Gly Asp Leu Gln Val Leu Ala Gln Lys Ala Glu Arg
    50                  55                  60

Ala Leu Pro Gly Gly Ser Ser Gly Gly Arg His Lys Gln Lys Ile Val
65                  70                  75                  80

Ala Pro Ala Lys Gln Leu Leu Gly Gly Ser Gly Gly Thr Asn Asn
                85                  90                  95

Val Arg Gly Asp Leu Gln Val Leu Ala Gln Lys Ala Glu Arg Ala Leu
            100                 105                 110

Pro Gly Gly Ser Ser Gly Gly Arg His Lys Gln Lys Ile Val Ala Pro
        115                 120                 125

Ala Lys Gln Leu Leu Gly Gly Gly Ser Lys Leu Ala Ser Thr Thr
    130                 135                 140

Ala Pro Lys Val Tyr Pro Leu Ser Ser Cys Cys Gly Asp Lys Ser Ser
145                 150                 155                 160

Ser Thr Val Thr Leu Gly Cys Leu Val Ser Ser Tyr Met Pro Glu Pro
                165                 170                 175

Val Thr Val Thr Trp Asn Ser Gly Ala Leu Lys Ser Gly Val His Thr
            180                 185                 190

Phe Pro Ala Val Leu Gln Ser Ser Gly Leu Tyr Ser Leu Ser Ser Met
        195                 200                 205

Val Thr Val Pro Ala Ser Ser Ser Gly Thr Gln Thr Phe Thr Cys Asn
    210                 215                 220

Val Ala His Pro Ala Ser Ser Thr Lys Val Asp Lys Ala Val Asp Pro
225                 230                 235                 240

Thr Cys Lys Pro Ser Pro Cys Asp Cys Cys Pro Pro Glu Leu Pro
                245                 250                 255

Gly Gly Pro Ser Val Phe Ile Phe Pro Pro Lys Pro Lys Asp Thr Leu
            260                 265                 270

Thr Ile Ser Gly Thr Pro Glu Val Thr Cys Val Val Val Asp Val Gly
        275                 280                 285

His Asp Asp Pro Glu Val Lys Phe Ser Trp Phe Val Asp Val Glu
    290                 295                 300

Val Asn Thr Ala Thr Thr Lys Pro Arg Glu Glu Gln Phe Asn Ser Thr
305                 310                 315                 320

Tyr Arg Val Val Ser Ala Leu Arg Ile Gln His Gln Asp Trp Thr Gly
                325                 330                 335
```

```
Gly Lys Glu Phe Lys Cys Lys Val His Asn Glu Gly Leu Pro Ala Pro
                340                 345                 350
Ile Val Arg Thr Ile Ser Arg Thr Lys Gly Pro Ala Arg Glu Pro Gln
                355                 360                 365
Val Tyr Val Leu Ala Pro Pro Gln Glu Glu Leu Ser Lys Ser Thr Val
                370                 375                 380
Ser Leu Thr Cys Met Val Thr Ser Phe Tyr Pro Asp Tyr Ile Ala Val
385                 390                 395                 400
Glu Trp Gln Arg Asn Gly Gln Pro Glu Ser Glu Asp Lys Tyr Gly Thr
                405                 410                 415
Thr Pro Pro Gln Leu Asp Ala Asp Ser Ser Tyr Phe Leu Tyr Ser Lys
                420                 425                 430
Leu Arg Val Asp Arg Asn Ser Trp Gln Glu Gly Asp Thr Tyr Thr Cys
                435                 440                 445
Val Val Met His Glu Ala Leu His Asn His Tyr Thr Gln Lys Ser Thr
                450                 455                 460
Ser Lys Ser Ala Gly Lys Gly Leu Ile Val Asp Thr Arg Asp Val Glu
465                 470                 475                 480
Glu Arg Val His Val Met Arg Lys Thr Lys Leu Ala Pro Thr Val Ala
                485                 490                 495
His Gly Val Phe Asn Pro Glu Phe Gly Pro Ala Ala Leu Ser Asn Lys
                500                 505                 510
Asp Pro Arg Leu Asn Glu Gly Val Val Leu Asp Asp Val Ile Phe Ser
                515                 520                 525
Lys His Lys Gly Asp Thr Arg Met Ser Glu Glu Asp Lys Ala Leu Phe
                530                 535                 540
Arg Arg Cys Ala Ala Asp Tyr Ala Ser Arg Leu His Ser Val Leu Gly
545                 550                 555                 560
Thr Ala Asn Ala Pro Leu Ser Val Tyr Glu Ala Ile Lys Gly Val Asp
                565                 570                 575
Gly Leu Asp Ala Met Glu Pro Asp Thr Ala Pro Gly Leu Pro Trp Ala
                580                 585                 590
Leu Gln Gly Lys Arg Arg Gly Ala Leu Ile Asp Phe Glu Asn Gly Thr
                595                 600                 605
Val Gly Pro Glu Val Glu Ala Ala Leu Lys Leu Met Glu Ser Arg Glu
                610                 615                 620
Tyr Lys Phe Val Cys Gln Thr Phe Leu Lys Asp Glu Ile Arg Pro Leu
625                 630                 635                 640
Glu Lys Val Arg Ala Gly Lys Thr Arg Ile Val Asp Val Leu Pro Val
                645                 650                 655
Glu His Ile Leu Tyr Thr Arg Met Met Ile Gly Arg Phe Cys Ala Gln
                660                 665                 670
Met His Ser Asn Asn Gly Pro Gln Ile Gly Ser Ala Val Gly Cys Asn
                675                 680                 685
Pro Asp Val Asp Trp Gln Arg Phe Gly Thr His Phe Ala Gln Tyr Lys
                690                 695                 700
Asn Val Trp Asp Val Asp Tyr Ser Ala Phe Asp Ala Asn His Cys Ser
705                 710                 715                 720
Asp Ala Met Asn Ile Met Phe Glu Glu Val Phe Arg Thr Glu Phe Gly
                725                 730                 735
Phe His Pro Asn Ala Glu Trp Ile Leu Lys Thr Leu Val Asn Thr Glu
                740                 745                 750
His Ala Tyr Glu Asn Lys Arg Ile Val Val Glu Gly Gly Met Pro Ser
```

```
                    755                 760                 765
Gly Cys Ser Ala Thr Ser Ile Ile Asn Thr Ile Leu Asn Asn Ile Tyr
    770                 775                 780

Val Leu Tyr Ala Leu Arg Arg His Tyr Glu Gly Val Glu Leu Asp Thr
785                 790                 795                 800

Tyr Thr Met Ile Ser Tyr Gly Asp Asp Ile Val Ala Ser Asp Tyr
                805                 810                 815

Asp Leu Asp Phe Glu Ala Leu Lys Pro His Phe Lys Ser Leu Gly Gln
            820                 825                 830

Thr Ile Thr Pro Ala Asp Lys Ser Asp Lys Gly Phe Val Leu Gly His
        835                 840                 845

Ser Ile Thr Asp Val Thr Phe Leu Lys Arg His Phe His Met Asp Tyr
850                 855                 860

Gly Thr Gly Phe Tyr Lys Pro Val Met Ala Ser Lys Thr Leu Glu Ala
865                 870                 875                 880

Ile Leu Ser Phe Ala Arg Arg Gly Thr Ile Gln Glu Lys Leu Ile Ser
                885                 890                 895

Val Ala Gly Leu Ala Val His Ser Gly Pro Asp Glu Tyr Arg Arg Leu
            900                 905                 910

Phe Glu Pro Phe Gln Gly Leu Phe Glu Ile Pro Ser Tyr Arg Ser Leu
        915                 920                 925

Tyr Leu Arg Trp Val Asn Ala Val Cys Gly Asp Ala
    930                 935                 940

<210> SEQ ID NO 42
<211> LENGTH: 2820
<212> TYPE: DNA
<213> ORGANISM: artificial
<220> FEATURE:
<223> OTHER INFORMATION: DNA sequence encoding the recombinant protein

<400> SEQUENCE: 42
atggtgagca acgtgcgcgg agatctccaa gtgctggctc aaaaagcaga acgtgcactg      60
ccgggcggct ctagtggcgg acgccataaa caaaagattg tcgcgccggc aaaacaactc     120
ctgggtggta gttctggagg caccaataac gtgcgcggcg atctgcaggt cctggcgcaa     180
aaagcggaac gtgctctgcc gggtggttcg agcggtggcc ggcataaaca gaaaattgtc     240
gcacctgcaa acagctgttt gggaggttcg agcggtggca ccaataatgt gcgcggcgac     300
ttgcaagtgc tggctcagaa ggcggaacgc gcattgcctg gtggttcgtc cggcggtcgg     360
cataaacaga aaattgtagc accggctaaa caactgctgg gcggtggagg ctctaagctt     420
gcctccacca cagccccgaa agtctaccct ctgagttctt gctgcgggga caagtccagc     480
tccaccgtga ccctgggctg cctggtctcc agctacatgc ccgagccggt gaccgtgacc     540
tggaactcgg gtgccctgaa gagcggcgtg cacaccttcc cggctgtcct tcagtcctcc     600
gggctgtact ctctcagcag catggtgacc gtgcccgcca gcagctcagg aacccagacc     660
ttcacctgca acgtagccca cccggccagc agcaccaagg tggacaaggc tgttgatccc     720
acatgcaaac atcacccctg tgactgttgc ccaccccctg agctccccgg aggaccctct     780
gtcttcatct tcccaccgaa acccaaggac accctcacaa tctcgggaac gcccgaggtc     840
acgtgtgtgt ggtggacgt gggccacgat gaccccgagg tgaagttctc ctggttcgtg     900
gacgacgtgg aggtaaacac agccacgacg aagccgagag aggagcagtt caacagcacc     960
taccgcgtgt cagcgccct gcgcatccag caccaggact ggactggagg aaaggagttc    1020
aagtgcaagg tccacaacga aggcctcccg gccccatcg tgaggaccat ctccaggacc    1080
```

```
aaagggccgg cccgggagcc gcaggtgtat gtcctggccc cacccccagga agagctcagc    1140 aaaagcacgg tcagcctcac ctgcatggtc accagcttct acccagacta catcgccgtg    1200
gagtggcaga gaaacgggca gcctgagtcg gaggacaagt acggcacgac cccgccccag    1260
ctggacgccg acagctccta cttcctgtac agcaagctca gggtggacag gaacagctgg    1320
caggaaggag acacctacac gtgtgtggtg atgcacgagg ccctgcacaa tcactacacg    1380
cagaagtcca cctctaagtc tgcgggtaaa gggttgatcg tcgacaccag agatgtggag    1440
gagcgtgtcc acgtgatgcg caaaaccaag ctcgcgccca ccgtggcgca cggtgtgttc    1500
aaccctgagt cgggcctgc cgctctgtcc aacaaggacc cgcgcctgaa cgaagggggtt    1560 gtccttgacg atgtcatttt ctccaaacac aaaggagata caaggatgtc tgaagaggac    1620
aaagcgctgt ttcggcgctg tgctgctgac tacgcgtcgc gtctacacag tgtgttgggg    1680
acagcaaacg ccccactgag tgtgtatgaa gccatcaaag cgtcgacgg acttgacgcc    1740 atggagccgg acacggcgcc cggtctcccc tgggctctcc aagggaaacg ccgcggcgcc    1800
ctgatcgact tcgaaaacgg caccgtcggg cctgaggttg aggcagcact caagctcatg    1860
gaaagccgcg agtacaaatt cgtctgccaa accttcctga aggacgaaat tcggccgcta    1920
gaaaaggtac gcgctggcaa gacacgcatt gtcgacgtgt tgcctgttga acacattctc    1980
tacaccagaa tgatgattgg cagattctgt gctcagatgc attcaaacaa cggaccgcaa    2040
attggatcag cggtcggttg taaccctgac gttgattggc aaagatttgg cacacatttc    2100
gcccagtaca aaaacgtgtg ggatgtggac tactcagcct ttgatgcaaa ccactgcagc    2160
gatgcgatga acatcatgtt cgaggaagtg ttccgcacgg agttcggatt ccacccgaac    2220
gccgagtgga ttctgaagac tctagtgaac acggagcacg cttacgagaa caagcgcatt    2280
gttgttgaag gtggaatgcc gtccggttgt tccgcaacaa gcatcatcaa cacaattttg    2340
aacaacatct acgtgcttta cgccctgcgt aggcactatg agggagtcga gctggacact    2400
tacaccatga tctcttatgg agacgacatc gtggtggcaa gtgactacga cctggacttt    2460
gaggctctca gcccccactt caagtccctt ggtcagacta tcactccggc cgacaaaagc    2520
gacaaaggtt ttgttcttgg tcactccata accgacgtca ctttcctcaa aagacacttc    2580
cacatggact acgaactgg gttttacaaa cctgtgatgg cctcgaagac ccttgaggcc    2640
atcctctcct ttgcacgccg tgggaccata caggagaagt tgatctccgt ggcaggactc    2700
gccgtccact ccggacctga tgaataccgg cgcctctttg agcccttcca aggcctcttc    2760
gagattccaa gctacagatc actttacctg cgatgggtga acgccgtgtg cggtgacgca    2820
```

<210> SEQ ID NO 43
<211> LENGTH: 20
<212> TYPE: PRT
<213> ORGANISM: Foot-and-mouth disease virus

<400> SEQUENCE: 43

Pro Ala Thr Arg Arg Gly Asp Leu Gly Ser Leu Ala Ala Arg Leu Ala
1               5                   10                  15

Ala Gln Leu Pro
            20

<210> SEQ ID NO 44
<211> LENGTH: 14
<212> TYPE: PRT
<213> ORGANISM: Foot-and-mouth disease virus

<400> SEQUENCE: 44

Arg His Lys Gln Lys Ile Ile Ala Pro Ala Lys Gln Leu Leu
1               5                   10

<210> SEQ ID NO 45
<211> LENGTH: 468
<212> TYPE: PRT
<213> ORGANISM: artificial
<220> FEATURE:
<223> OTHER INFORMATION: amino acid sequence of the recombinant protein

<400> SEQUENCE: 45

Met Pro Ala Thr Arg Arg Gly Asp Leu Gly Ser Leu Ala Ala Arg Leu
1               5                   10                  15

Ala Ala Gln Leu Pro Gly Gly Ser Ser Gly Gly Arg His Lys Gln Lys
                20                  25                  30

Ile Ile Ala Pro Ala Lys Gln Leu Leu Gly Gly Ser Ser Gly Gly Pro
            35                  40                  45

Ala Thr Arg Arg Gly Asp Leu Gly Ser Leu Ala Ala Arg Leu Ala Ala
        50                  55                  60

Gln Leu Pro Gly Gly Ser Ser Gly Gly Arg His Lys Gln Lys Ile Ile
65                  70                  75                  80

Ala Pro Ala Lys Gln Leu Leu Gly Gly Ser Ser Gly Gly Pro Ala Thr
                85                  90                  95

Arg Arg Gly Asp Leu Gly Ser Leu Ala Ala Arg Leu Ala Ala Gln Leu
                100                 105                 110

Pro Gly Gly Ser Ser Gly Gly Arg His Lys Gln Lys Ile Ile Ala Pro
            115                 120                 125

Ala Lys Gln Leu Leu Gly Gly Gly Ser Leu Ala Pro Lys Thr
130                 135                 140

Ala Pro Ser Val Tyr Pro Leu Ala Pro Cys Gly Arg Asp Thr Ser Gly
145                 150                 155                 160

Pro Asn Val Ala Leu Gly Cys Leu Ala Ser Ser Tyr Phe Pro Glu Pro
                165                 170                 175

Val Thr Met Thr Trp Asn Ser Gly Ala Leu Thr Ser Gly Val His Thr
            180                 185                 190

Phe Pro Ser Val Leu Gln Pro Ser Gly Leu Tyr Ser Leu Ser Ser Met
        195                 200                 205

Val Thr Val Pro Ala Ser Ser Leu Ser Ser Lys Ser Tyr Thr Cys Asn
210                 215                 220

Val Asn His Pro Ala Thr Thr Thr Lys Val Asp Lys Arg Val Gly Thr
225                 230                 235                 240

Lys Thr Lys Pro Pro Cys Pro Thr Cys Pro Gly Cys Glu Val Ala Gly
                245                 250                 255

Pro Ser Val Phe Ile Phe Pro Pro Lys Pro Lys Asp Thr Leu Met Ile
            260                 265                 270

Ser Gln Thr Pro Glu Val Thr Cys Val Val Val Asp Val Ser Lys Glu
        275                 280                 285

His Ala Glu Val Gln Phe Ser Trp Tyr Val Asp Gly Val Glu Val His
    290                 295                 300

Thr Ala Glu Thr Arg Pro Lys Glu Glu Gln Phe Asn Ser Thr Tyr Arg
305                 310                 315                 320

Val Val Ser Val Leu Pro Ile Gln His Gln Asp Trp Leu Lys Gly Lys
                325                 330                 335

Glu Phe Lys Cys Lys Val Asn Asn Val Asp Leu Pro Ala Pro Ile Thr
            340                 345                 350

```
Arg Thr Ile Ser Lys Ala Ile Gly Gln Ser Arg Glu Pro Gln Val Tyr
        355                 360                 365

Thr Leu Pro Pro Pro Ala Glu Glu Leu Ser Arg Ser Lys Val Thr Val
    370                 375                 380

Thr Cys Leu Val Ile Gly Phe Tyr Pro Pro Asp Ile His Val Glu Trp
385                 390                 395                 400

Lys Ser Asn Gly Gln Pro Glu Pro Gly Asn Tyr Arg Thr Thr Pro
                405                 410                 415

Pro Gln Gln Asp Val Asp Gly Thr Phe Phe Leu Tyr Ser Lys Leu Ala
                420                 425                 430

Val Asp Lys Ala Arg Trp Asp His Gly Glu Thr Phe Glu Cys Ala Val
                435                 440                 445

Met His Glu Ala Leu His Asn His Tyr Thr Gln Lys Ser Ile Ser Lys
450                 455                 460

Thr Gln Gly Lys
465

<210> SEQ ID NO 46
<211> LENGTH: 1380
<212> TYPE: DNA
<213> ORGANISM: artificial
<220> FEATURE:
<223> OTHER INFORMATION: DNA sequence encoding the recombinant protein

<400> SEQUENCE: 46
atgcctgcaa cacggcgagg tgacttgggg tctctcgcgg cgaggctcgc cgcacagctt      60
cctggcggct ctagtggcgg aagacacaag cagaaaatca ttgcccctgc aaagcaactc     120
ctgggtggta gttctggagg ccctgcaaca cggcgaggtg acttggggtc tctcgcggcg     180
aggctcgccg cacagcttcc tggtggttcg agcggtggag acacaagca gaaaatcatt     240 gcccctgcaa agcaactcct gggaggttcg agcggtggcc ctgcaacacg gcgaggtgac     300
ttggggtctc tcgcggcgag gctcgccgca cagcttcctg gtggttcgtc cggcggtaga     360
cacaagcaga aaatcattgc ccctgcaaag caactcctgg cggtggagg ctctaagctt      420 gcccccaaga cggcccccatc ggtctaccct ctggccccct gcggcaggga cacgtctggc     480
cctaacgtgg ccttgggctg cctggcctca agctacttcc ccgagccagt gaccatgacc     540
tggaactcgg gcgccctgac cagtggcgtg cataccttcc catccgtcct gcagccgtca     600
gggctctact ccctcagcag catggtgacc gtgccggcca gcagcctgtc agcaagagc      660 tacacctgca atgtcaacca cccggccacc accaccaagg tggacaagcg tgttggaaca     720
aagaccaaac caccatgtcc cacatgccca ggctgtgaag tggccgggcc ctcggtcttc     780
atcttccctc caaacccaa ggacaccctc atgatctccc agaccccga ggtcacgtgc      840 gtggtggtgg acgtcagcaa ggagcacgcc gaggtccagt tcctggta cgtggacggc      900 gtagaggtgc acacgccga cgagacca aggaggagc agttcaacag cacctaccgt        960
gtggtcagcg tcctgcccat ccagcaccag gactggctga aggggaagga gttcaagtgc    1020
aaggtcaaca acgtagacct cccagcccccc atcacgagga ccatctccaa ggctataggg    1080
cagagccggg agccgcaggt gtacaccctg cccccacccg ccgaggagct gtccaggagc    1140
aaagtcaccg taacctgcct ggtcattggc ttctacccac tgacatcca tgttgagtgg    1200 aagagcaacg gacagccgga gccagagggc aattaccgca ccaccccgcc ccagcaggac    1260
gtggacggga ccttcttcct gtacagcaag ctcgcggtgg acaaggcaag atgggaccat    1320
ggagaaacat ttgagtgtgc ggtgatgcac gaggctctgc acaaccacta cacccagaag    1380
```

<210> SEQ ID NO 47
<211> LENGTH: 938
<212> TYPE: PRT
<213> ORGANISM: artificial
<220> FEATURE:
<223> OTHER INFORMATION: amino acid sequence of the recombinant protein

<400> SEQUENCE: 47

```
Met Pro Ala Thr Arg Arg Gly Asp Leu Gly Ser Leu Ala Ala Arg Leu
 1               5                  10                  15

Ala Ala Gln Leu Pro Gly Gly Ser Ser Gly Gly Arg His Lys Gln Lys
             20                  25                  30

Ile Ile Ala Pro Ala Lys Gln Leu Leu Gly Gly Ser Ser Gly Gly Pro
         35                  40                  45

Ala Thr Arg Arg Gly Asp Leu Gly Ser Leu Ala Ala Arg Leu Ala Ala
     50                  55                  60

Gln Leu Pro Gly Gly Ser Ser Gly Gly Arg His Lys Gln Lys Ile Ile
 65                  70                  75                  80

Ala Pro Ala Lys Gln Leu Leu Gly Gly Ser Ser Gly Gly Pro Ala Thr
                 85                  90                  95

Arg Arg Gly Asp Leu Gly Ser Leu Ala Ala Arg Leu Ala Ala Gln Leu
            100                 105                 110

Pro Gly Gly Ser Ser Gly Gly Arg His Lys Gln Lys Ile Ile Ala Pro
        115                 120                 125

Ala Lys Gln Leu Leu Gly Gly Gly Ser Lys Leu Ala Pro Lys Thr
    130                 135                 140

Ala Pro Ser Val Tyr Pro Leu Ala Pro Cys Gly Arg Asp Thr Ser Gly
145                 150                 155                 160

Pro Asn Val Ala Leu Gly Cys Leu Ala Ser Ser Tyr Phe Pro Glu Pro
                165                 170                 175

Val Thr Met Thr Trp Asn Ser Gly Ala Leu Thr Ser Gly Val His Thr
            180                 185                 190

Phe Pro Ser Val Leu Gln Pro Ser Gly Leu Tyr Ser Leu Ser Ser Met
        195                 200                 205

Val Thr Val Pro Ala Ser Ser Leu Ser Ser Lys Ser Tyr Thr Cys Asn
    210                 215                 220

Val Asn His Pro Ala Thr Thr Thr Lys Val Asp Lys Arg Val Gly Thr
225                 230                 235                 240

Lys Thr Lys Pro Pro Cys Pro Thr Cys Pro Gly Cys Glu Val Ala Gly
                245                 250                 255

Pro Ser Val Phe Ile Phe Pro Pro Lys Pro Lys Asp Thr Leu Met Ile
            260                 265                 270

Ser Gln Thr Pro Glu Val Thr Cys Val Val Asp Val Ser Lys Glu
        275                 280                 285

His Ala Glu Val Gln Phe Ser Trp Tyr Val Asp Gly Val Glu Val His
    290                 295                 300

Thr Ala Glu Thr Arg Pro Lys Glu Glu Gln Phe Asn Ser Thr Tyr Arg
305                 310                 315                 320

Val Val Ser Val Leu Pro Ile Gln His Gln Asp Trp Leu Lys Gly Lys
                325                 330                 335

Glu Phe Lys Cys Lys Val Asn Asn Val Asp Leu Pro Ala Pro Ile Thr
            340                 345                 350

Arg Thr Ile Ser Lys Ala Ile Gly Gln Ser Arg Glu Pro Gln Val Tyr
        355                 360                 365

Thr Leu Pro Pro Pro Ala Glu Glu Leu Ser Arg Ser Lys Val Thr Val
```

```
              370                 375                 380
Thr Cys Leu Val Ile Gly Phe Tyr Pro Pro Asp Ile His Val Glu Trp
385                 390                 395                 400

Lys Ser Asn Gly Gln Pro Glu Pro Glu Gly Asn Tyr Arg Thr Thr Pro
                405                 410                 415

Pro Gln Gln Asp Val Asp Gly Thr Phe Phe Leu Tyr Ser Lys Leu Ala
                420                 425                 430

Val Asp Lys Ala Arg Trp Asp His Gly Glu Thr Phe Glu Cys Ala Val
                435                 440                 445

Met His Glu Ala Leu His Asn His Tyr Thr Gln Lys Ser Ile Ser Lys
                450                 455                 460

Thr Gln Gly Lys Gly Leu Ile Val Asp Thr Arg Asp Val Glu Glu Arg
465                 470                 475                 480

Val His Val Met Arg Lys Thr Lys Leu Ala Pro Thr Val Ala His Gly
                485                 490                 495

Val Phe Asn Pro Glu Phe Gly Pro Ala Ala Leu Ser Asn Lys Asp Pro
                500                 505                 510

Arg Leu Asn Glu Gly Val Val Leu Asp Asp Val Ile Phe Ser Lys His
                515                 520                 525

Lys Gly Asp Thr Arg Met Ser Glu Glu Asp Lys Ala Leu Phe Arg Arg
530                 535                 540

Cys Ala Ala Asp Tyr Ala Ser Arg Leu His Ser Val Leu Gly Thr Ala
545                 550                 555                 560

Asn Ala Pro Leu Ser Val Tyr Glu Ala Ile Lys Gly Val Asp Gly Leu
                565                 570                 575

Asp Ala Met Glu Pro Asp Thr Ala Pro Gly Leu Pro Trp Ala Leu Gln
                580                 585                 590

Gly Lys Arg Arg Gly Ala Leu Ile Asp Phe Glu Asn Gly Thr Val Gly
                595                 600                 605

Pro Glu Val Glu Ala Ala Leu Lys Leu Met Glu Ser Arg Glu Tyr Lys
                610                 615                 620

Phe Val Cys Gln Thr Phe Leu Lys Asp Glu Ile Arg Pro Leu Glu Lys
625                 630                 635                 640

Val Arg Ala Gly Lys Thr Arg Ile Val Asp Val Leu Pro Val Glu His
                645                 650                 655

Ile Leu Tyr Thr Arg Met Met Ile Gly Arg Phe Cys Ala Gln Met His
                660                 665                 670

Ser Asn Asn Gly Pro Gln Ile Gly Ser Ala Val Gly Cys Asn Pro Asp
                675                 680                 685

Val Asp Trp Gln Arg Phe Gly Thr His Phe Ala Gln Tyr Lys Asn Val
                690                 695                 700

Trp Asp Val Asp Tyr Ser Ala Phe Asp Ala Asn His Cys Ser Asp Ala
705                 710                 715                 720

Met Asn Ile Met Phe Glu Glu Val Phe Arg Thr Glu Phe Gly Phe His
                725                 730                 735

Pro Asn Ala Glu Trp Ile Leu Lys Thr Leu Val Asn Thr Glu His Ala
                740                 745                 750

Tyr Glu Asn Lys Arg Ile Val Val Glu Gly Gly Met Pro Ser Gly Cys
                755                 760                 765

Ser Ala Thr Ser Ile Ile Asn Thr Ile Leu Asn Asn Ile Tyr Val Leu
                770                 775                 780

Tyr Ala Leu Arg Arg His Tyr Glu Gly Val Glu Leu Asp Thr Tyr Thr
785                 790                 795                 800
```

```
Met Ile Ser Tyr Gly Asp Asp Ile Val Val Ala Ser Asp Tyr Asp Leu
            805                 810                 815

Asp Phe Glu Ala Leu Lys Pro His Phe Lys Ser Leu Gly Gln Thr Ile
        820                 825                 830

Thr Pro Ala Asp Lys Ser Asp Lys Gly Phe Val Leu Gly His Ser Ile
        835                 840                 845

Thr Asp Val Thr Phe Leu Lys Arg His Phe His Met Asp Tyr Gly Thr
    850                 855                 860

Gly Phe Tyr Lys Pro Val Met Ala Ser Lys Thr Leu Glu Ala Ile Leu
865                 870                 875                 880

Ser Phe Ala Arg Arg Gly Thr Ile Gln Glu Lys Leu Ile Ser Val Ala
                885                 890                 895

Gly Leu Ala Val His Ser Gly Pro Asp Glu Tyr Arg Arg Leu Phe Glu
            900                 905                 910

Pro Phe Gln Gly Leu Phe Glu Ile Pro Ser Tyr Arg Ser Leu Tyr Leu
        915                 920                 925

Arg Trp Val Asn Ala Val Cys Gly Asp Ala
    930                 935

<210> SEQ ID NO 48
<211> LENGTH: 2814
<212> TYPE: DNA
<213> ORGANISM: artificial
<220> FEATURE:
<223> OTHER INFORMATION: DNA sequence encoding the recombinant protein

<400> SEQUENCE: 48
atgcctgcaa cacggcgagg tgacttgggg tctctcgcgg cgaggctcgc cgcacagctt      60
cctggcggct ctagtggcgg aagacacaag cagaaaatca ttgcccctgc aaagcaactc     120
ctgggtggta gttctggagg ccctgcaaca cggcgaggtg acttggggtc tctcgcggcg     180
aggctcgccg cacagcttcc tggtggttcg agcggtggca gacacaagca gaaaatcatt     240
gcccctgcaa agcaactcct gggaggttcg agcggtggcc tgcaacacg gcgaggtgac     300 ttggggtctc tcgcggcgag gctcgccgca cagcttcctg gtggttcgtc cggcggtaga     360
cacaagcaga aaatcattgc ccctgcaaag caactcctgg gcggtggagg ctctaagctt     420
gcccccaaga cggccccatc ggtctaccct ctggcccct gcggcaggga cacgtctggc     480
cctaacgtgg ccttgggctg cctggcctca agctacttcc ccgagccagt gaccatgacc     540
tggaactcgg gcgccctgac cagtggcgtg catcccttcc catccgtcct gcagccgtca     600
gggctctact ccctcagcag catggtgacc gtgccggcca gcagcctgtc cagcaagagc     660
tacacctgca atgtcaacca cccggccacc accaccaagg tggacaagcg tgttggaaca     720
aagaccaaac caccatgtcc cacatgccca ggctgtgaag tggccgggcc ctcggtcttc     780
atcttccctc caaaacccaa ggacacccct atgatctccc agaccccga ggtcacgtgc     840 gtggtggtgg acgtcagcaa ggagcacgcc gaggtccagt tcctggta cgtggacggc     900 gtagaggtgc acacggccga gacgagacca aggaggagc agttcaacag cacctaccgt     960
gtggtcagcg tcctgcccat ccagcaccag gactggctga aggggaagga gttcaagtgc    1020
aaggtcaaca acgtagacct cccagccccc atcacgagga ccatctccaa ggctataggg    1080
cagagccggg agccgcaggt gtacaccctg cccccaccg ccgaggagct gtccaggagc    1140
aaagtcaccg taacctgcct ggtcattggc ttctacccac ctgacatcca tgttgagtgg    1200
aagagcaacg gacagccgga gccagagggc aattaccgca ccaccccgcc ccagcaggac    1260
gtggacggga ccttcttcct gtacagcaag ctcgcggtgg acaaggcaag atgggaccat    1320
```

```
ggagaaacat tgagtgtgc ggtgatgcac gaggctctgc acaaccacta cacccagaag    1380
tccatctcca agactcaggg taaagggttg atcgtcgaca ccagagatgt ggaggagcgt    1440
gtccacgtga tgcgcaaaac caagctcgcg cccaccgtgg cgcacggtgt gttcaaccct    1500
gagttcgggc ctgccgctct gtccaacaag gacccgcgcc tgaacgaagg ggttgtcctt    1560
gacgatgtca ttttctccaa acacaaagga gatacaagga tgtctgaaga ggacaaagcg    1620
ctgtttcggc gctgtgctgc tgactacgcg tcgcgtctac acagtgtgtt ggggacagca    1680
aacgccccac tgagtgtgta tgaagccatc aaaggcgtcg acggacttga cgccatggag    1740
ccggacacgg cgcccggtct ccctgggct ctccaaggga acgccgcgg cgccctgatc    1800 gacttcgaaa acggcaccgt cgggcctgag gttgaggcag cactcaagct catggaaagc    1860
cgcgagtaca aattcgtctg ccaaaccttc ctgaaggacg aaattcggcc gctagaaaag    1920
gtacgcgctg gcaagacacg cattgtcgac gtgttgcctg ttgaacacat tctctacacc    1980
agaatgatga ttggcagatt ctgtgctcag atgcattcaa acaacggacc gcaaattgga    2040
tcagcggtcg gttgtaaccc tgacgttgat tggcaaagat ttggcacaca tttcgcccag    2100
tacaaaaacg tgtgggatgt ggactactca gcctttgatg caaaccactg cagcgatgcg    2160
atgaacatca tgttcgagga agtgttccgc acggagttcg gattccaccc gaacgccgag    2220
tggattctga agactctagt gaacacggag cacgcttacg agaacaagcg cattgttgtt    2280
gaaggtggaa tgccgtccgg ttgttccgca acaagcatca tcaacacaat tttgaacaac    2340
atctacgtgc tttacgccct gcgtaggcac tatgagggag tcgagctgga cacttacacc    2400
atgatctctt atggagacga catcgtggtg gcaagtgact acgacctgga ctttgaggct    2460
ctcaagcccc acttcaagtc ccttggtcag actatcactc cggccgacaa aagcgacaaa    2520
ggttttgttc ttggtcactc cataaccgac gtcactttcc tcaaaagaca cttccacatg    2580
gactacggaa ctgggtttta caaacctgtg atggcctcga agacccttga ggccatcctc    2640
tcctttgcac gccgtgggac catacaggag aagttgatct ccgtggcagg actcgccgtc    2700
cactccggac ctgatgaata ccggcgcctc tttgagccct tccaaggcct cttcgagatt    2760
ccaagctaca gatcacttta cctgcgatgg gtgaacgccg tgtgcggtga cgca          2814
```